US009789208B2

(12) United States Patent
Kularatne

(10) Patent No.: US 9,789,208 B2
(45) Date of Patent: *Oct. 17, 2017

(54) SYNTHESIS AND COMPOSITION OF AMINO ACID LINKING GROUPS CONJUGATED TO COMPOUNDS USED FOR THE TARGETED IMAGING OF TUMORS

(71) Applicant: Purdue Research Foundation, West Lafayette, IN (US)

(72) Inventor: Sumith A. Kularatne, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/259,719

(22) Filed: Sep. 8, 2016

(65) Prior Publication Data

US 2016/0375153 A1     Dec. 29, 2016

Related U.S. Application Data

(63) Continuation-in-part of application No. 14/953,928, filed on Nov. 30, 2015, which is a continuation of application No. 14/715,799, filed on May 19, 2015, now Pat. No. 9,341,629, which is a continuation of application No. 14/207,130, filed on Mar. 12, 2014, now Pat. No. 9,061,057, which is a continuation of application No. 14/010,098, filed on Aug. 26, 2013, now Pat. No. 9,333,270.

(60) Provisional application No. 61/791,921, filed on Mar. 15, 2013.

(51) Int. Cl.
*A61B 5/00* (2006.01)
*A61B 8/00* (2006.01)
*A61B 10/00* (2006.01)
*A61K 49/00* (2006.01)

(52) U.S. Cl.
CPC ...... *A61K 49/0052* (2013.01); *A61K 49/0032* (2013.01); *A61K 49/0034* (2013.01); *A61K 49/001* (2013.01)

(58) Field of Classification Search
None
See application file for complete search history.

(56) References Cited

U.S. PATENT DOCUMENTS 4,337,339 A    6/1982  Farina et al.
7,547,721 B1   6/2009  Miwa et al.
9,061,057 B2 * 6/2015  Kularatne .......... A61K 49/0052
9,333,270 B2 * 5/2016  Low .................. A61K 49/0052
9,341,629 B2 * 5/2016  Kularatne .......... A61K 49/0052
2006/0063247 A1  3/2006  Lugade et al.
2006/0280688 A1 12/2006  Kovar et al.
2012/0003151 A1  1/2012  Low et al.

FOREIGN PATENT DOCUMENTS

WO       200016810        3/2000
WO       200143781  A1    6/2001
WO       200174382  A1   10/2001
WO       2002098885 A1   12/2002
WO       2007139815 A2   12/2007
WO       2008057437 A2    5/2008
WO       2010033733 A1    3/2010
WO       2010102238 A1    9/2010
WO       2011150392 A1   12/2011

OTHER PUBLICATIONS

Australian Examination Report dated Aug. 22, 2016 for Australian Patent Application No. 2013383382.
Milstein et al., "Statistical Approach for Detection and Localization of a Fluorescing Mouse Tumor in Intralipid", Applied Optics, 2005, vol. 44, No. 12 , pp. 2300-2310.
Moon et al., "Enhanced Tumor Detection Using a Folate Receptor-Targeted Near-Infrared Fluorochrome Conjugate", Bioconjugate Chem, 2003, vol. 14, pp. 539-545.
European Extended Search Report dated Sep. 16, 2016 for European Patent Application No. 13878809.
Chinese Office Action dated Feb. 17, 2017 for Chinese Patent Application No. CN 201380074692.8.
Office Action for Israel Application No. 240673 (PCT/US2013/056629) dated Jun. 4, 2017.
First Examination Report for New Zealand Application No. 711297 dated May 10, 2017.
Zaheer, A. et al. (Molecular Imaging, 2002. vol. 1(4), pp. 354-364.
Zaheer, A. et al. (Nature Biotechnology, 2001, vol. 19, pp. 1148-1154.
Communication pursuant to Article 94(3) EPC for application 13878809.6 dated May 17, 2017.

* cited by examiner

*Primary Examiner* — Michael G Hartley
*Assistant Examiner* — Melissa Perreira
(74) *Attorney, Agent, or Firm* — McAndrews, Held & Malloy, Ltd.

(57) ABSTRACT

The present disclosure relates to compounds that are useful as near-infrared fluorescence probes, wherein the compounds include i) a pteroyl ligand that binds to a target receptor protein, ii) a dye molecule, and iii) a linker molecule that comprises an amino acid or derivative thereof. The disclosure further describes methods and compositions for incorporating the compounds as used for the targeted imaging of tumors. Conjugation of the amino acid linking groups increase specificity and detection of the compound. Methods and compositions for use thereof in diagnostic imaging are contemplated.

5 Claims, 26 Drawing Sheets

SYNTHESIS AND COMPOSITION OF AMINO ACID LINKING GROUPS CONJUGATED TO COMPOUNDS USED FOR THE TARGETED IMAGING OF TUMORS

RELATED APPLICATIONS

The present patent application is a Continuation-in-Part of U.S. patent application Ser. No. 14/953,928, filed Nov. 30, 2015, which is a continuation of U.S. patent application Ser. No. 14/715,799, filed May 19, 2015, now U.S. Pat. No. 9,341,629, which is a continuation of U.S. patent application Ser. No. 14/207,130, filed Mar. 12, 2014, now U.S. Pat. No. 9,061,057, which is a continuation of U.S. patent application Ser. No. 14/010,098, filed Aug. 26, 2013, now U.S. Pat. No. 9,333,270, which is related to and claims priority benefit of U.S. Provisional Patent Application No. 61/791,921, filed Mar. 15, 2013, all of which are hereby incorporated by reference in their entirety into this disclosure.

FIELD OF THE DISCLOSURE

The present disclosure is in the area of diagnostics. This disclosure provides methods of synthesizing and utilizing amino acid linking groups that are conjugated to a compound used for the targeted imaging of tumors. Conjugation of the amino acid linking groups increase specificity and detection of the compound. Methods and compositions for use thereof in diagnostic imaging are contemplated.

BACKGROUND OF THE DISCLOSURE

Surgical removal of malignant disease constitutes one of the most common and effective therapeutic for primary treatment for cancer. Resection of all detectable malignant lesions results in no detectable return of the disease in approximately 50% of all cancer patients[1] and may extend life expectancy or reduce morbidity for patients in whom recurrence of the cancer is seen. Not surprisingly, surgical methods for achieving more quantitative cytoreduction are now receiving greater scrutiny.

Resection of all detectable malignant lesions results in no detectable return of the disease in approximately 50% of all cancer patients and may extend life expectancy or reduce morbidity for patients in whom recurrence of the cancer is seen. Given the importance of total resection of the malignant lesions, it is beneficial to ensure that the malignant lesions are accurately and completely identified. Identification of malignant tissue during surgery is currently accomplished by three methods. First, many tumor masses and nodules can be visually detected based on abnormal color, texture, and/or morphology. Thus, a tumor mass may exhibit variegated color, appear asymmetric with an irregular border, or protrude from the contours of the healthy organ. A malignant mass may also be recognized tactilely due to differences in plasticity, elasticity or solidity from adjacent healthy tissues. Finally, a few cancer foci can be located intraoperatively using fluorescent dyes that flow passively from the primary tumor into draining lymph nodes. In this latter methodology, fluorescent (sentinel) lymph nodes can be visually identified, resected and examined to determine whether cancer cells have metastasized to these lymph nodes.

Despite the recognition of the importance of removal of tumor and the availability of certain identification techniques for visualizing tumor mass, many malignant nodules still escape detection, leading to disease recurrence and often death. Thus, there is a need for improved tumor identification. This motivation has led to introduction of two new approaches for intraoperative visualization of malignant disease. In the first, a quenched fluorescent dye is injected systemically into the tumor-bearing animal, and release of the quenching moiety by a tumor-specific enzyme, pH change, or change in redox potential is exploited to selectively activate fluorescence within the malignant mass. In the second approach, a fluorescent dye is conjugated to a tumor-specific targeting ligand that causes the attached dye to accumulate in cancers that over-express the ligand's receptor. Examples of tumor targeting ligands used for this latter purpose include folic acid, which exhibits specificity for folate receptor (FR) positive cancers of the ovary, kidney, lung, endometrium, breast, and colon, and DUPA, which can deliver attached fluorescent dyes selectively to cells expressing prostate-specific membrane antigen (PSMA), i.e. prostate cancers and the neovasculature of other solid tumors. Beneficially, one folate-targeted fluorescent dye (folate-fluorescein or EC17) has been recently tested intra-operatively in human ovarian cancer patients. In this study, ~5× more malignant lesions were removed with the aid of the tumor-targeted fluorescent dye than without it, and all resected fluorescent lesions were confirmed by pathology to be malignant.

Conventional fluorescent techniques use probes in the visible light spectrum (~400-600 nm), which is not optimal for intra-operative image-guided surgery as it is associated with a relatively high level of nonspecific background light due to collagen in the tissues. Hence the signal to noise ratio from these conventional compounds is low. Moreover, the absorption of visible light by biological chromophores, in particular hemoglobin, limits the penetration depth to a few millimeters. Thus tumors that are buried deeper than a few millimeters in the tissue may remain undetected. Moreover ionization equilibrium of fluorescein (pKa=6.4) leads to pH-dependent absorption and emission over the range of 5 to 9. Therefore, the fluorescence of fluorescein-based dyes is quenched at low pH (below pH 5).

For example, the potential use of EC17 dye for a more widespread use in optical imaging for the characterization and measurement diseased tissue in a clinical setting has been hampered by the major drawback of that the attached dye (fluorescein) emits fluorescence in the visible range. This makes EC17 and related dyes poor for in vivo use in tissues because tissues typically autofluoresce strongly in the visible range, and light penetrates tissue poorly. Moreover, EC17 (folate-ethelenediamine-fluorescein isothiocynate) consists a thiourea linker. It is well known that thiourea compounds have low shelf life due to the instability of the thiourea linkage. Thus, a compound such as EC17 is not optimal for use in optical imaging because of this unstability and the related decomposition of the decomposition of thiourea bridge.

The combination of light absorption by hemoglobin in the visible light spectrum (<600 nm) and water and lipids in the IR range (>900 nm), offers an optical imaging window from approximately 650-900 nm in which the absorption coefficient of tissue is at a minimum. A suitable alternative to dyes that emit light in the visible range would be to develop dyes that can be used in the near infra-red (NIR) range because light in the near infrared region induces very little autofluorescence and permeates tissue much more efficiently. Another benefit to near-IR fluorescent technology is that the background from the scattered light from the excitation source is greatly reduced since the scattering intensity is proportional to the inverse fourth power of the wavelength.

Low background fluorescence is necessary for highly sensitive detection. Furthermore, the optically transparent window in the near-IR region (650 nm to 900 nm) in biological tissue makes NIR fluorescence a valuable technology for in vivo imaging and subcellular detection applications that require the transmission of light through biological components.

While the use of light in the NIR range for deeper tissue imaging is preferable to light in the visible spectrum, the NIR imaging dyes currently used in the art suffer from a number of challenges and disadvantages such as a susceptibility to photobleach, poor chemical stability, absorbance and emission spectra that fall within the same range as many physiological molecules (resulting in high background signal and autofluorescence). Moreover, most of the NIR dyes are not stable during the synthesis, especially conjugating to a ligand with an amine linker, leading to multiple unwanted side products. Therefore, taking ligand-targeted NIR imaging agent for clinic can be expensive. Thus, current imaging methods that utilize NIR fluorescent probes are not effective in deep tissue imaging (>5 mm from the surface), in quantifying fluorescence signal in mammalian tissues, or in production cost that increase preclinical-to-clinical translational time.

Two promising approaches to fluorescence-guided surgery are currently under intense investigation for use in the clinic. In one method, an activatable NIR fluorescent probe, which is minimally fluorescent in the steady state due to its proximity to an attached quencher, becomes highly fluorescent upon release of the quencher in malignant tissue. One of the most commonly used release mechanisms involves incorporation of a peptide sequence between the dye and the quencher that can be specifically cleaved by a tumor-enriched protease (i.e. cathepsins, caspases and matrix metalloproteinases). A major advantage of this strategy lies in the absence of fluorescence in tissues that lack the activating enzyme, allowing tissues along the excretion pathway (e.g. kidneys, bladder, liver) to remain nonfluorescent unless they fortuitously express the cleaving enzyme. Such tumor-activated NIR dyes can also generate substantial fluorescence in the tumor mass as long as the malignant lesion is enriched in the cleaving protease and the released dye is retained in the tumor. The major disadvantage of this methodology arises from the poor tumor specificities of many of the relevant hydrolases (most of which are also expressed in healthy tissues undergoing natural remodeling or experiencing inflammation). Moreover, the abundance of the desired proteases may vary among tumor masses, leading to slow or no activation of fluorescence in some malignant lesions and rapid development of fluorescence in others.

Thus, there remains a need for a dye substance that can be used to specifically target diseased tissue and has increased stability and brightness for use in vivo for tissue imaging.

BRIEF SUMMARY OF THE DISCLOSURE

This disclosure provides a method for synthesizing amino acid linking groups that are conjugated to a compound used for the targeted imaging of tumors and lymph nodes. In certain embodiments, this disclosure relates to a compound or a salt derivative thereof, that comprises a folate or pteroyl ligand, a linking group, and a fluorescent dye. In certain embodiments, the linking group can be an amino acid, an isomer, a derivative, or a racemic mixture thereof. In other aspects, the fluorescent dye is selected from the group consisting of LS288, IR800, SP054, S0121, KODAK, S2076 and S0456.

In some aspects, this disclosure provides a method of conjugating an amino acid linking group to a fluorescent dye, wherein the amino acid can be tyrosine, serine, theronine, lysine, arginine, asparagine, glutamine, cysteine, selenocysteine, isomers, and the derivatives thereof. In certain embodiments, the amino acid, isomers, or the derivatives thereof, contain an —OH, —NH$_2$, or —SH functional group that upon addition of the fluorescent dye in slight molar excess produces the conjugation of fluorescent group with the amino acid, isomer, or the derivatives thereof. In other embodiments, the amino acid, isomers, or the derivatives thereof, contains an —OH functional group that upon synthesis generates an ether bond with the fluorescent dye that increases the brightness and detection of the compound. In some embodiments, this disclosure relates to the conjugation of the amino acid linking group with the fluorescent dye, wherein the amino acid, isomers, or the derivatives thereof, contains an —SH, —SeH, —PoH, or —TeH functional group that upon synthesis generates a C—S, C—Se, C—Po, or C—Te bond with the fluorescent dye. In some aspects, this disclosure relates to the conjugation of the amino acid linking group to a fluorescent dye that has an absorption and emission maxima between about 500 nm and about 900 nm. In other aspects, the amino acid linking group is conjugated to a fluorescent dye that has an absorption and emission maxima between about 600 nm and about 800 nm.

In additional embodiments, this disclosure provides a method for conjugating the amino acid linking group to a folate ligand, wherein the amino acid linking group is tyrosine, serine, theronine, lysine, arginine, asparagine, glutamine, cysteine, selenocysteine, isomers or the derivatives thereof, and is conjugated to folate through a dipeptide bond. In additional aspects, this disclosure provides a method of conjugating the linking group with a folate ligand, wherein the linking group is tyrosine, serine, theronine, lysine, arginine, asparagine, glutamine, cysteine, selenocysteine, isomers, or the derivatives thereof, and is conjugated to folate through a homo-oligopeptide bond. In other embodiments, this disclosure relates to a method of conjugating a pteroyl ligand to an amino acid linking group, wherein the linking group is tyrosine, serine, theronine, lysine, arginine, asparagine, glutamine, cysteine, selenocysteine, isomers or the derivatives thereof. In certain aspects, the carboxylic acid of the linking group is bound to the alpha carbon of any amino acid, hence increasing the specificity of the compound for targeted receptors. In some embodiments, the amino acid linking group contributes specificity to the compound, wherein the observed binding affinity of the compound to targeted receptors is folate receptor.

In additional aspects, the compound is highly selective for targeting to tumor cells expressing the target receptor.

In other embodiments, this disclosure relates to the use of a compound designated, Pte-Tyr-50456 (OTL-0038) for image guided surgery, tumor imaging, lymph node imaging, inflammatory diseases, atherosclerosis, infection diseases, forensic applications, mineral applications, dental, gel staining, DNA sequencing, nerve staining, or plastic surgery. In other aspects, the Pte-Tyr-50456 derivative can be Pte-D-Tyr-S0456, Pte-homoTyr-S0456, Pte-beta-homo-Tyr-S0456, Pte-(NMe)-Tyr-S0456, Pte-Tyr(OMe)-S0456, Pte-Tyr(OBn)-S0456, Pte-NHNH-Tyr-OAc-S0456, salts, or derivatives thereof.

In other aspects, this disclosure provides a method of synthesizing the compound, wherein a protecting group is used to avoid undesired reactivity with groups other than the amino groups that might generate unwanted compounds.

The methods provided in this disclosure produce a final compound with a yield of over 98% purity.

In certain aspects, this disclosure relates to a compound used for the targeted imaging of tumors, wherein the compound could be used for research, diagnostic, or therapeutic purposes. In other embodiments, this disclosure provides a composition comprising an imaging compound and a pharmaceutically acceptable carrier, excipient, diluents, or salts.

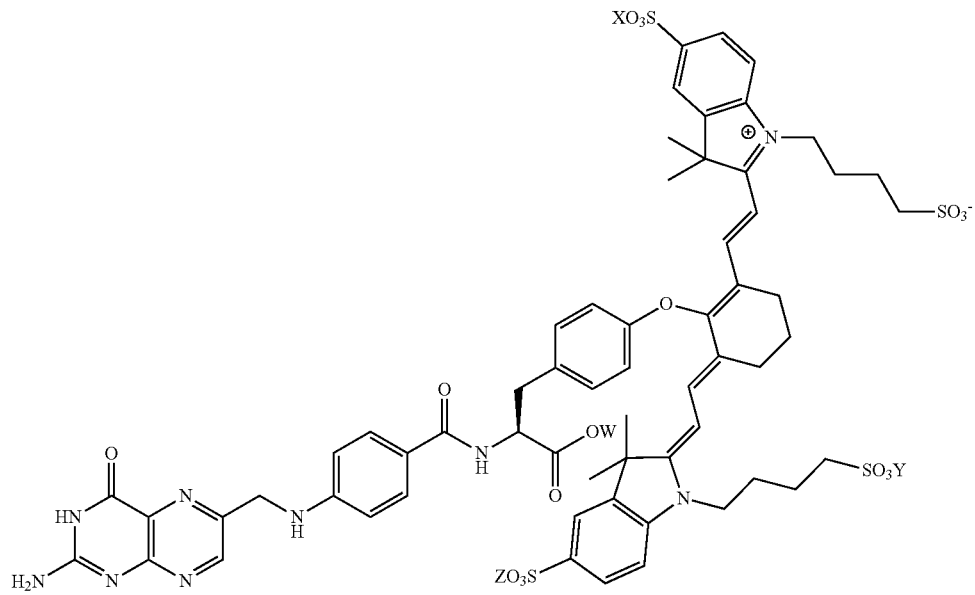

wherein W, X, Y, or Z is H, Na, or $NH_4^+$,

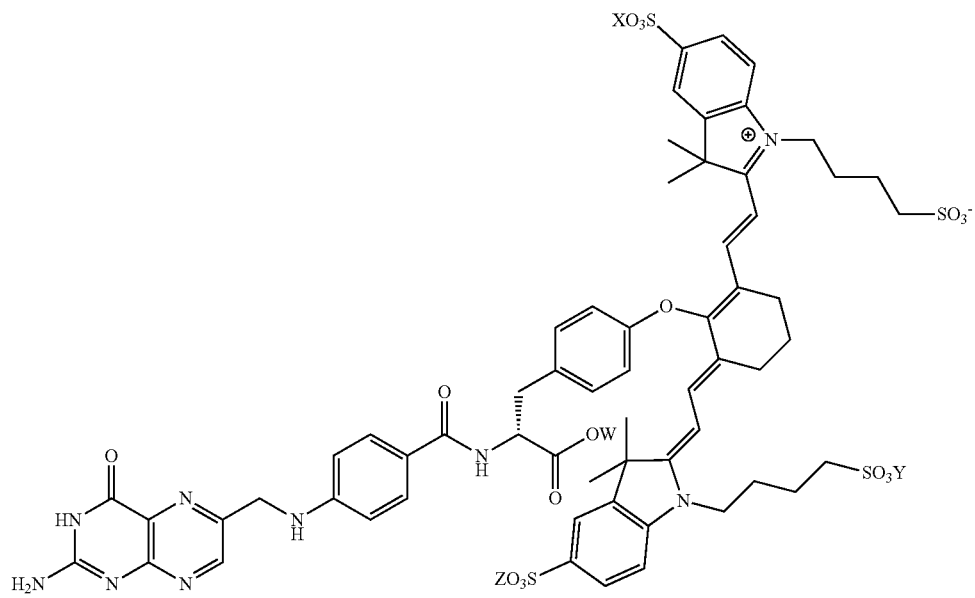

wherein W, X, Y, or Z is H, Na, or $NH_4^+$,

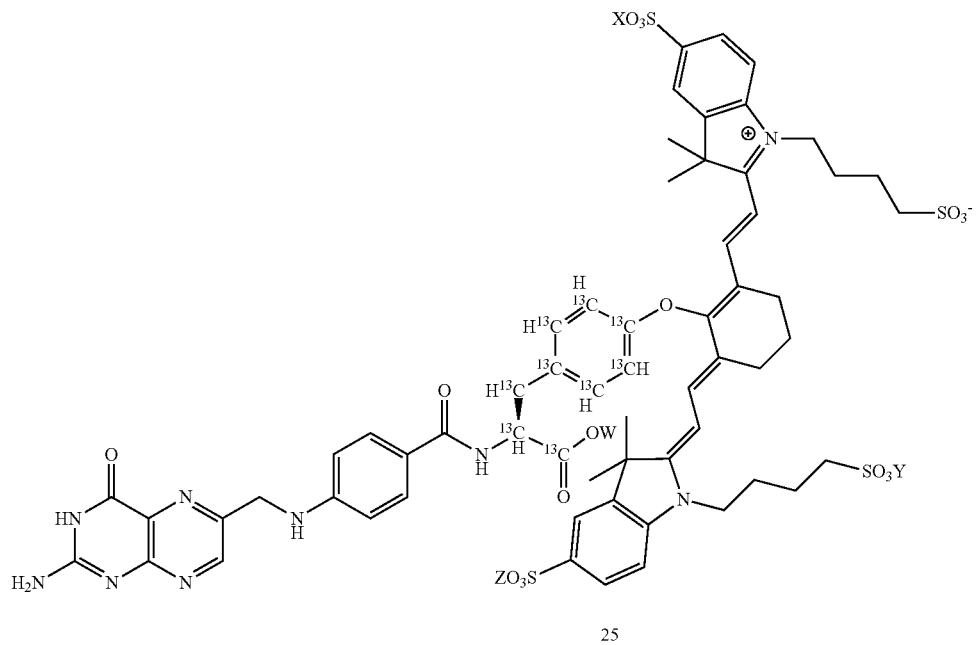

wherein W, X, Y, or Z is H, Na, or $NH_4^+$,

BRIEF DESCRIPTION OF SEVERAL VIEWS OF THE DRAWINGS

FIG. 5D depicts a gray scale fluorescence of the mouse of FIG. 5a.

DETAILED DESCRIPTION OF THE DISCLOSURE

Figure 1:
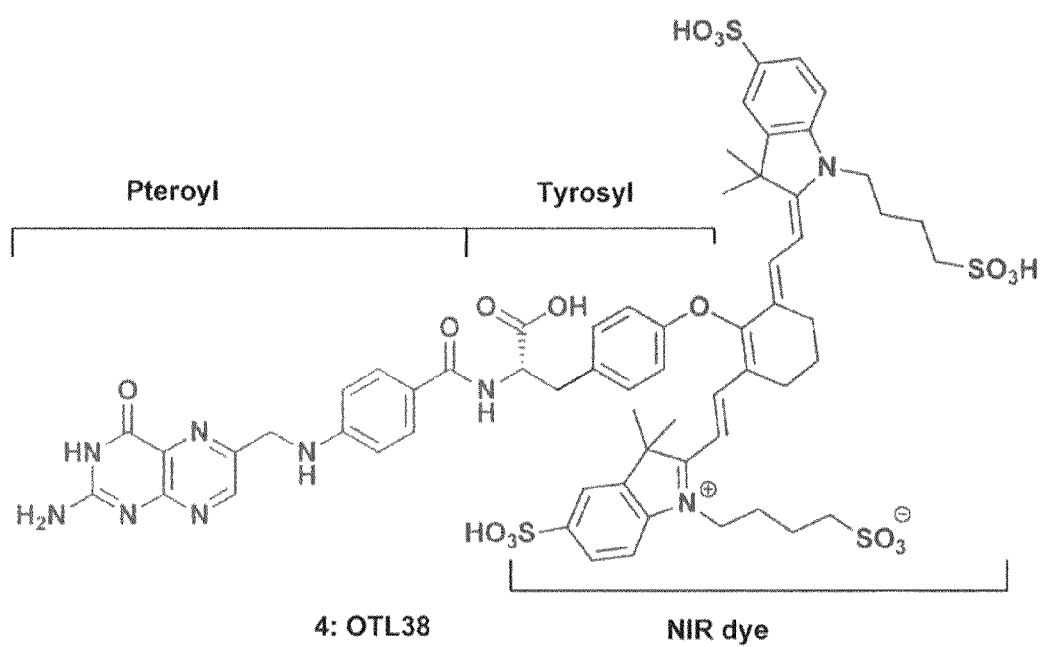
FIG. 1 depicts the design of OTL38.
Figure 2:
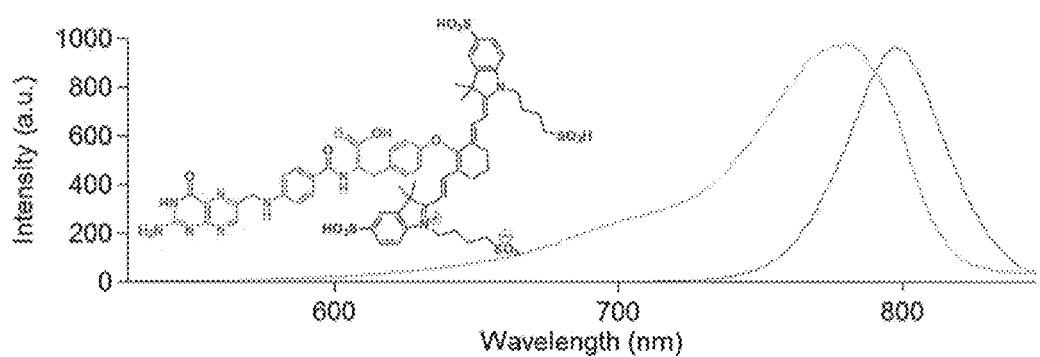
FIG. 2 depicts the chemical structures, excitation and emission spectra of OTL38.
Figure 3A:
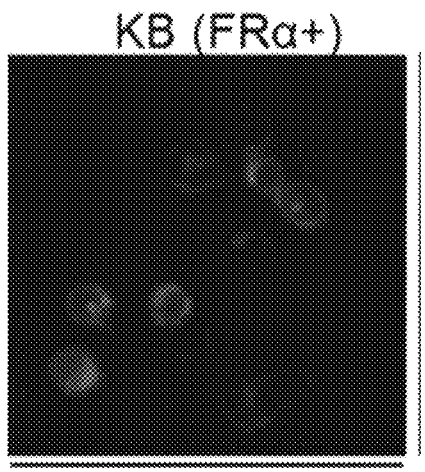
FIG. 3A depicts binding and internalization of OTL38 to human cervical cancer (KB-FR$^+$) cells by confocal microscopy.
Figure 3B:
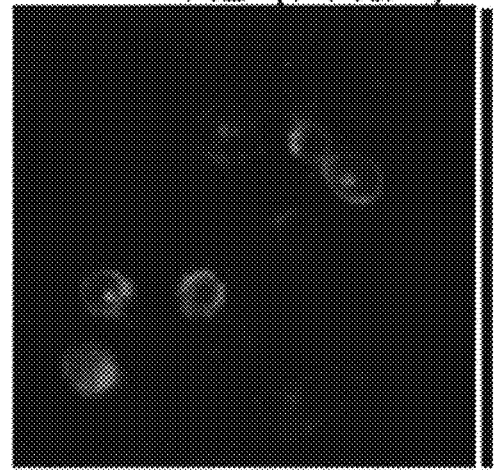
FIG. 3B depicts binding and internalization of OTL38 to human cervical cancer (KB-FR$^+$) cells by confocal microscopy.
Figure 3C:
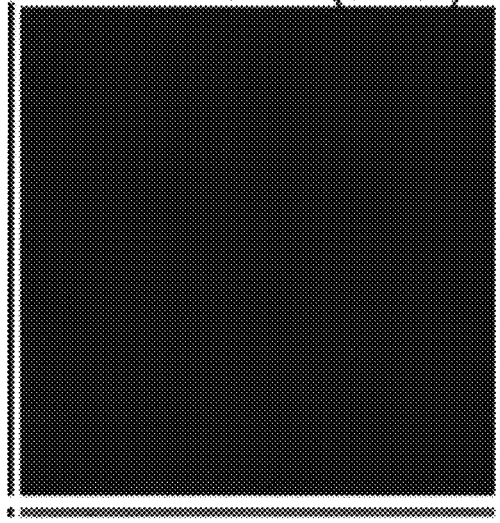
FIG. 3C depicts binding and internalization of OTL38 to human lung cancer (A549-FR$^-$) cells by confocal microscopy.
Figure 3D:
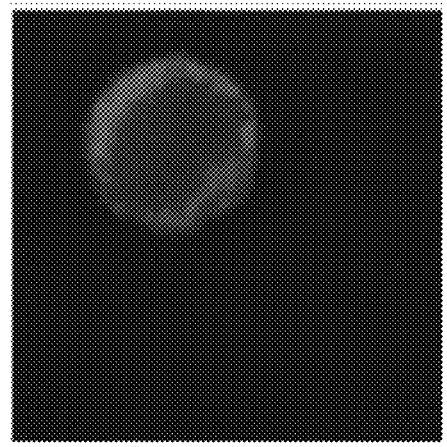
FIG. 3D depicts binding and internalization of OTL38 to human breast cancer (MDA-MB 231-FR$^+$) cells by confocal microscopy.
Figure 3E:
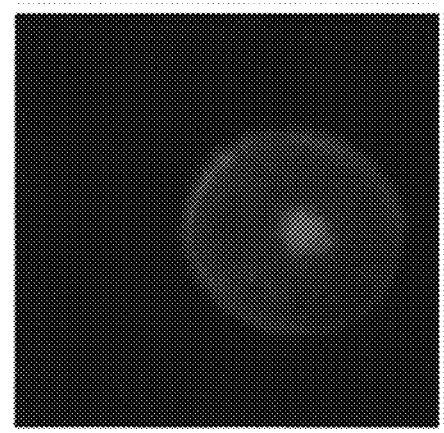
FIG. 3E depicts binding and internalization of OTL38 to human ovarian cancer (SKOV3-FR$^+$) cells by confocal microscopy.
Figure 3F:
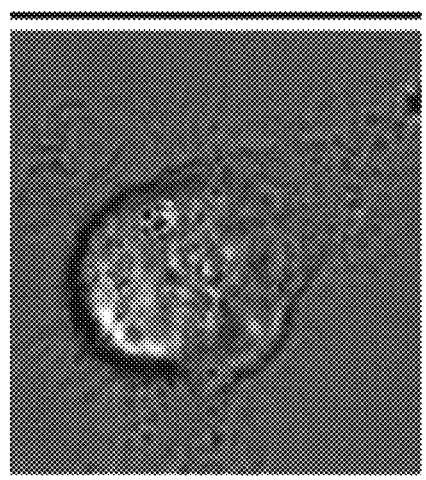
FIG. 3F depicts binding and internalization of OTL38 to human lung cancer (A549-FR$^-$) cells by bright field image from confocal microscopy.

Surgery is one of the best therapies for all the solid tumors, such as prostate, ovarian, lung, breast, colon, and pancreatic cancer. While surgery is effective in 50% of patients with solid tumors in the US, chemo- and radiotherapy alone are effective in less than 5% of all cancer patients. Over 700,000 patients undergo cancer surgery every year in the US and 40% of surgical patients have a recurrence of locoregional disease within 5 years. Despite major advances in the oncology field over the last decade, there remain significant hurdles to overcome in the field. For example, it remains difficult to achieve complete resection of the primary tumor with negative margins, removal of the lymph nodes harboring metastatic cancer cells and identification of satellite disease. Achieving improvements in these three cases not only improves disease clearance but also guides decisions regarding postoperative chemotherapy and radiation. While non-targeted fluorescent dyes have been shown to passively accumulate in some tumors, the resulting tumor-to-background ratios are often poor and the boundaries between malignant and healthy tissues can be difficult to define. Although ligand targeted fluorescence dyes (e.g., EC17: Folate-EDA-FITC) have been used for imaging a tissue, those dyes have been ineffective as they would not penetrate deep tissue and hence only identified the specific cells on the surface of a tissue rather than deeper within the tissue sample. In addition, it has been shown that the excitation and emission spectra of these previous fluorescence dyes was such that it produced significant background noise such that the targeted tissue was not easily detected. In addition, as discussed in the background above, fluorescein-based dyes have the disadvantages that of low shelf-life stability. EC17 easily decomposes as a result of the instability of the thiourea bridge in that compound. In addition, as EC17 uses fluorescein which has the drawback of a relatively high level of nonspecific background noise from collagen in the tissues surrounding the imaging site. Moreover, the absorption of visible light by biological chromophores, in particular hemoglobin, further limits the usefulness of dyes that incorporate fluorescein. This means that conventional dyes cannot readily detect tumors that may be buried deeper than a few millimeters in the tissue. Furthermore, fluorescence from fluorescein is quenched at low pH (below pH 5)

In order for a dye material to be useful in detecting and guiding surgery or providing other tissue imaging it is important to overcome these drawbacks.

Several criteria were considered in preparation of conjugates including near infrared dyes. Ease of synthesis and chemical stability were primary chemical attributes. Spectral properties, such as absorption and emission spectra and quantum yield, were considered. Several biological properties were evaluated, such as binding affinity in cell studies, whole body animal imaging using mice with tumors, and biodistribution. Specifically for biodistribution several aspects were considered including dead mice after 2 hours per oral distribution, live mice imaging and dose escalation. Finally, safety considerations were taken including Maximum Tolerance Dose (MTD), ImmunoHistoChemical (IHC) analysis, and general clinical pathology analysis.

The present disclosure provides pteroyl conjugates of near infrared dyes that are stable, fluoresce in the infrared range, and penetrate deep within targeted tissue to produce a specific and bright identification of areas of tissue that express folate receptor. More specifically, the pteroyl conjugates are linked to the near infrared dyes through an amino acid linker. Even more specifically, it has been found that where the amino acid linker is tyrosine or a derivative of tyrosine, the intensity of the fluorescence of the dye is maintained or even enhanced.

An amino acid is defined as including an amine functional group linked to a carboxylic acid functional group, and a side-chain specific to each amino acid. An alpha amino acid is any compound of the general formula $R^5CH(NH_2)COOH$ (α-amino acid), wherein $R^5$ is selected from the group consisting of H or any known amino acid side chain.

A beta amino acid is defined as including an amine functional group linked at a beta carbon and a carboxylic acid functional group linked at the alpha carbon. A beta homo amino acid is defined as including an amine functional group linked at a beta carbon, a carboxylic acid functional group linked at the alpha carbon and a side-chain starting at either the alpha carbon or the beta carbon wherein the side-chain is bound to another amino acid.

Naturally occurring amino acids can be divided into the following four groups: (1) acidic amino acids, (2) basic amino acids, (3) neutral polar amino acids, and (4) neutral nonpolar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, tyrosine, asparagine, and glutamine; and (4) neutral nonpolar (hydrophobic) amino acids such as alanine, leucine, isoleucine, valine, proline, phenylalanine, tryptophan, and methionine.

Conserved substitution for an amino acid within a naturally occurring amino acid sequence can be selected from other members of the group to which the naturally occurring amino acid belongs. For example, the aliphatic side chains group of amino acids is glycine, alanine, valine, leucine, and isoleucine. Conserved substitution of naturally occurring amino acid valine includes use of glycine, alanine, leucine, or isoleucine.

The aliphatic-hydroxyl side chain group of amino acids is serine and threonine. The amide-containing side chain group of amino acids is asparagine and glutamine. The aromatic side chain group of amino acids is phenylalanine, tyrosine, and tryptophan. The basic side chain group of amino acids is lysine, arginine, and histidine. The sulfur-containing side chain group of amino acids having is cysteine and methionine. Examples of naturally conservative amino acids substitutions are: valine for leucine, serine for threonine, phenylalanine for tyrosine, lysine for arginine, cysteine for methionine, and asparagine for glutamine.

In preferred embodiments, it is shown herein that such pteroyl conjugates specifically target to tumor cells within a tissue. Moreover, the intensity of the fluorescence in greater than the intensity of previously observed with other near infrared dyes that are targeted with folate for folate receptor positive tumors. This increased intensity allows the targeting and clear identification of smaller areas of biological samples (e.g., smaller tumors) from a tissue being monitored. In addition, the increased intensity of the compounds of the present disclosure provides the added advantage that lower doses/quantities of the dye can be administered and still produces meaningful results. Thus, the compounds of the present disclosure lead to more economical imaging techniques. Moreover, there is an added advantaged that a lower dose of the compounds of the disclosure as compared to conventional imaging compounds minimizes the toxicity and other side effects that are attendant with administration of foreign materials to a body.

Furthermore, identification of small tumors will lead to a more accurate and more effective resection of the primary tumor to produce negative margins, as well as accurate identification and removal of the lymph nodes harboring metastatic cancer cells and identification of satellite disease. Each of these advantages positively correlates with a better clinical outcome for the patient being treated.

In specific experiments, it was found that use of amino acids other than tyrosine as the linker resulted in loss of near infrared fluorescence. For example, see discussion of Scheme I. Specifically note the synthetic pathway lead to undesired by-product 4 as major product that does not have NIR properties However, it is contemplated that in addition to tyrosine and tyrosine derivatives, a pteroyl conjugate of a near infrared dye with cysteine or cysteine derivatives also may be useful. Furthermore, it is contemplated that a direct linkage of the pteroyl or folate moiety to the dye or linkage of the dye to pteroic acid or folic acid through an amine linker also produces a loss of intensity of the fluorescence from the conjugate whereas the presence of the tyrosine or tyrosine derivative as the linking moiety between the pteroyl (targeting moiety) and the near infrared dye (the fluorescing moiety) is beneficial to maintain or enhance the fluorescence of the conjugated compound. Tyrosine-based compounds of the disclosure do not require an extra amine linker to conjugate the S0456 and further because conjugation through the phenol moiety of the tyrosine leads to enhanced fluorescence.

The compounds can be used with fluorescence-mediated molecular tomographic imaging systems, such as those designed to detect near-infrared fluorescence activation in deep tissues. The compounds provide molecular and tissue specificity, yield high fluorescence contrast, brighter fluorescence signal, and reduce background autofluorescence, allowing for improved early detection and molecular target assessment of diseased tissue in vivo (e.g., cancers). The compounds can be used for deep tissue three dimensional imaging, targeted surgery, and methods for quantifying the amount of a target cell type in a biological sample.

Compounds

In an aspect the disclosure relates to compounds comprising the formula, Formula (I):

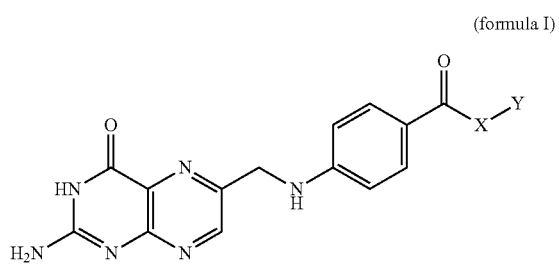

(formula I)

wherein:

X is an amino acid or a derivative thereof, and

Y is a dye that has a fluorescence excitation and emission spectra in the near infra-red range, and said compound maintains or enhances the fluorescence of Y.

In some embodiments, the amino acid or amino acid derivative induces a shift in the electronic emission spectrum, the electronic absorption spectrum, or both the electronic emission and absorption spectrum, relative to the electronic spectra of the unmodified dye molecule. Suitably, the shift in the electronic spectrum is a bathochromic shift (i.e., shift to longer wavelength/lower frequency) that helps to improve the detection of the compound in the near infrared (NIR) spectral window and/or reduce the amount of background signal, auto-fluorescence, interferences from the tissue surrounding the area being visualized. More specifically, this shift in electronic spectrum is particularly observed with NIR dyes that comprise electronegative atoms that are incorporated into the 6-membered ring. Thus, in certain embodiments the amino acid or amino acid (X) derivative comprises an electron-rich moiety such as, for example, oxygen, sulfur, or nitrogen. Non-limiting examples of such amino acids can include cysteine, methionine, threonine, serine, tyrosine, phenylalanine, tryptophan, histidine, lysine, arginine, aspartic acid, glutamic acid, asparagine, and glutamine, or derivatives thereof.

In embodiments of this aspect, the disclosure provides compounds of Formulas (I)a, (I)b, (I)c, and (I)d:

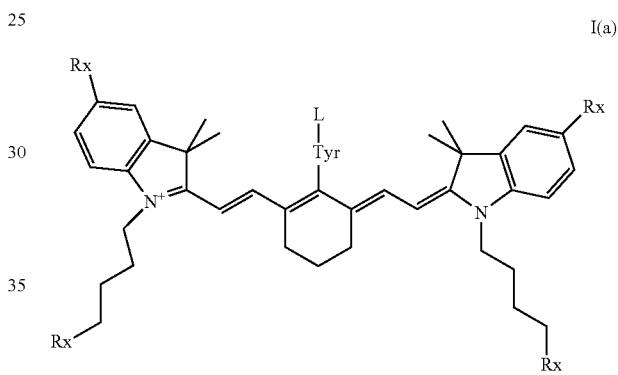

I(a)

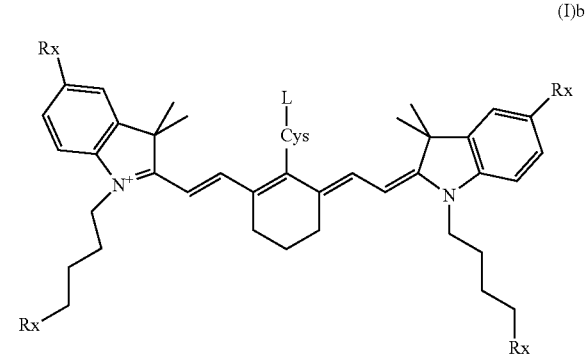

(I)b

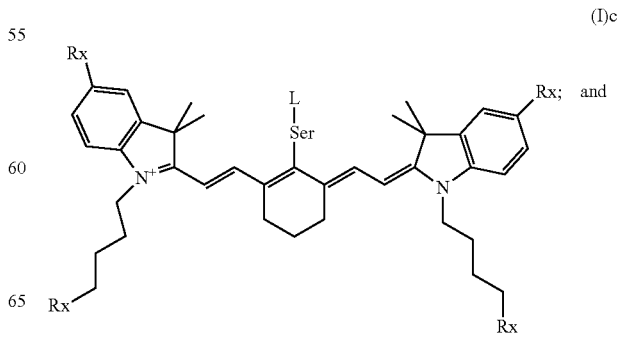

(I)c; and

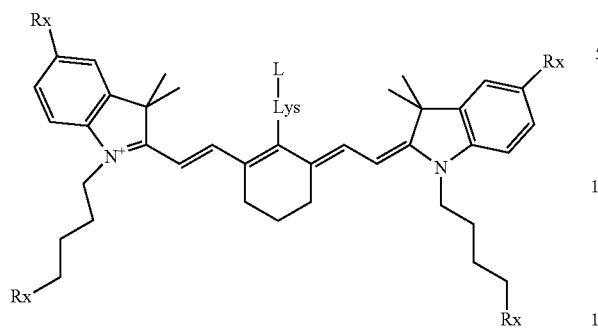

wherein the Tyr, Cys, Ser, and Lys groups indicate a tyrosine, a cysteine, a serine, and a lysine amino acid residue, respectively, or derivatives thereof, and L is preferably a pteroyl or folate and Rx each comprises an independently selected solubilizing group that is optionally absent.

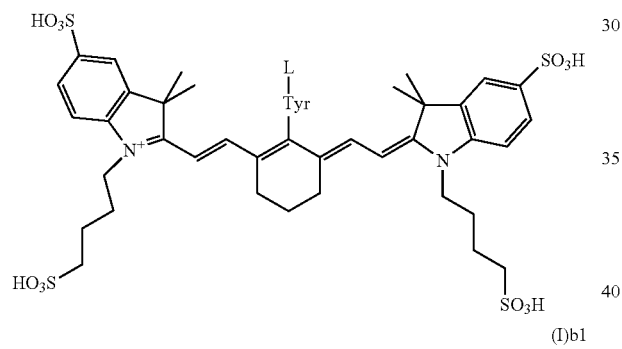

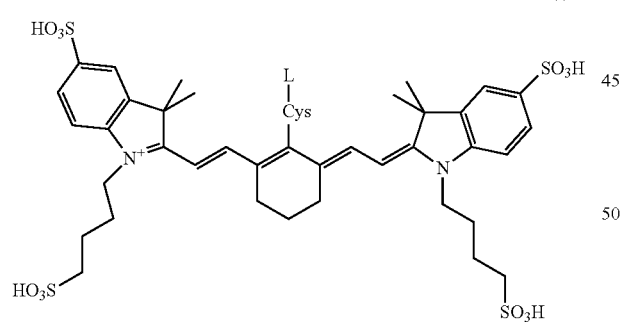

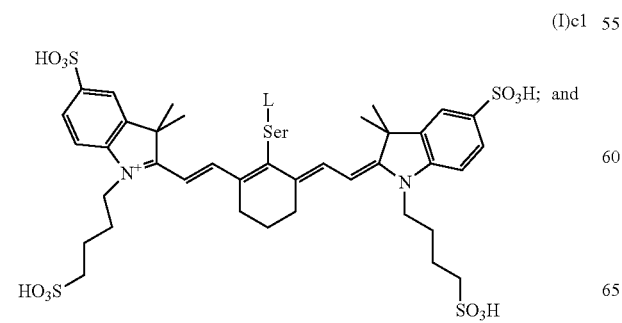

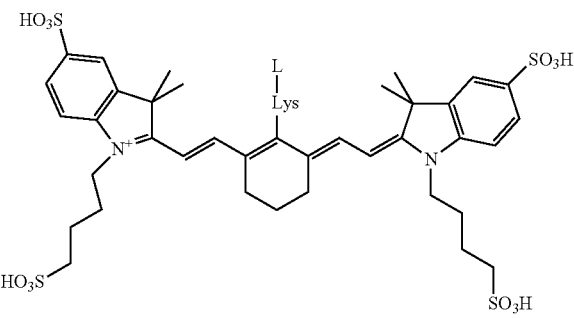

Wherein the Tyr, Cys, Ser, and Lys groups indicate a tyrosine, a cysteine, a serine, and a lysine amino acid residue, respectively, or derivatives thereof, and L is preferably a pteroyl or folate. Preferably, L is pteroyl.

In specific preferred embodiments the disclosure provides a compound of Formula I(a), wherein Tyr is selected from the group consisting of:

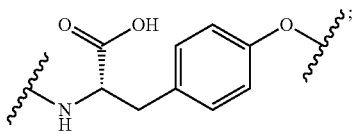

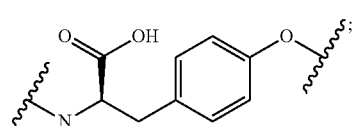

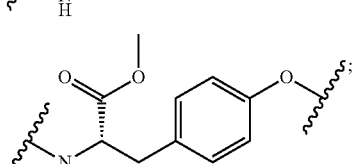

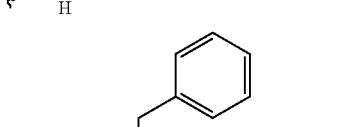

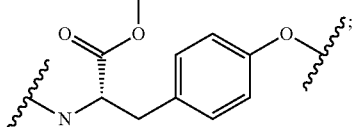

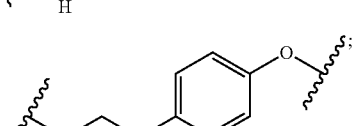

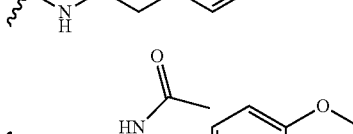

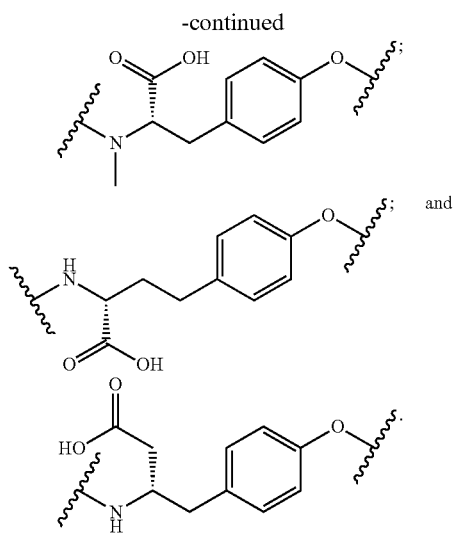

Suitably, the compounds disclosed herein have a maximum light absorption wavelengths in the near infrared region of between about 650 nm and 1000 nm, for example and preferably, at approximately 800 nm.

In specific preferred embodiments, the compounds disclosed herein include a ligand (L) that is effective to target the compound to a particular cell or tissue type and allow for imaging of that targeted cell or tissue. It is preferable the L is either pteroyl moiety or folate moiety and more preferable that L is pteroyl moiety. However, it is contemplated that the skilled person may use some other ligand L to target the compounds to a particular cell surface protein or receptor protein of interest. In specific and preferred embodiments, the ligand comprises pteroyl:

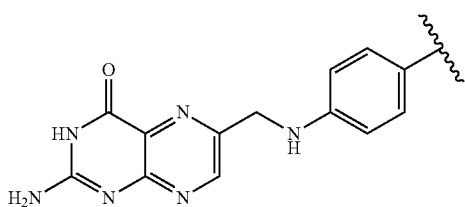 [SMILES: *c1ccc(NCc2cnc3nc(N)[nH]c(=O)c3n2)cc1]

Methods of Use

As noted herein above, there is a need for near infrared dye compounds that specifically target to regions within a tissue. This is so that the compounds may be used in imaging techniques and to assist in the diagnosis and therapeutic intervention of disease. As discussed in detail above, the compounds provided herein are useful as dyes and imaging agents in the NIR region of the light spectrum. As such, the compounds have broad applicability to any number of imaging, diagnostic, and targeted therapeutic methods.

In specific embodiments, the present disclosure relates to methods that incorporate at least one of the compounds disclosed herein (e.g., of Formula I, I(a), I(b), I(c), and/or I(d)). can be used to specifically and sensitively identify tumors within a tissue. More specifically, the identified tumors may then be therapeutically resected through surgical methods. In this manner, the compounds of the present disclosure may be useful in fluorescence guided surgical resection of tumors, lymph nodes, and the like. Alternatively, the compounds of the present disclosure may readily be used in whole body imaging in which the compound is administered to a subject and the localization of the fluorescence facilitates identification of a tumor site.

In this manner, the compounds of the present disclosure can be used for the in vivo identification of diseased tissue in a subject in need thereof. The disclosure method includes irradiating an in vivo body part of the subject containing diseased tissue with light having at least one excitation wavelength in the near infrared range from about 600 nm to about 1000 nm. Fluorescence emanating from a compound of the present disclosure administered to the subject and which has specifically bound to and/or been taken up by the diseased tissue in the body part, in response to the at least one excitation wavelength is directly viewed to determine the location and/or surface area of the diseased tissue in the subject.

Light having a wavelength range from 600 nm and 850 nm lies within the near infrared range of the spectrum, in contrast to visible light, which lies within the range from about 401 nm to 500 nm. Therefore, the excitation light used in practice of the disclosure diagnostic methods will contain at least one wavelength of light to illuminates the tissue at the infrared wavelength to excite the compounds in order that the fluorescence obtained from the area having uptake of the compounds of the present disclosure is clearly visible and distinct from the auto-fluorescence of the surrounding tissue. The excitation light may be monochromatic or polychromatic. In this manner, the compounds of the present disclosure are advantageous as they eliminate the need for use of filtering mechanisms that would be used to obtain a desired diagnostic image if the fluorescent probe is one that fluoresces at wavelengths below 600 nm. In this manner, the compounds of the present disclosure avoid obscured diagnostic images that are produced as a result of excitation light of wavelengths that would be reflected from healthy tissue and cause loss of resolution of the fluorescent image.

Operating rooms for surgical procedures can be equipped with an overhead light that produces wavelengths of light in the optical emitting spectrum useful in practice of disclosure diagnostic methods, such as a lamps that produce light in the appropriate wavelength. Such a light can be utilized in the practice of the disclosure diagnostic methods merely by turning out the other lights in the operating room (to eliminate extraneous light that would be visibly reflected from tissue in the body part under investigation) and shining the excitation light of near infrared wavelength into the body cavity or surgically created opening so that the fluorescent image received directly by the eye of the observer (e.g., the surgeon) is predominantly the fluorescent image emanating from the fluorophore(s) in the field of vision. Light emanating from a source in the 600 nm and 850 nm range, preferably 750 nm-850 nm range would be used in accomplishing the goal of direct visualization by the observer so that light reflecting from the body part, other than that from the fluorescing moiet(ies), is minimized or eliminated.

Accordingly, in disclosure diagnostic methods, the diseased tissue (and bound or taken-up targeting construct) is "exposed" to the excitation light (e.g, by surgically created opening or endoscopic delivery of the light to an interior location. The disclosed method is particularly suited to in vivo detection of diseased tissue located at an interior site in the subject, such as within a natural body cavity or a surgically created opening, where the diseased tissue is "in plain view" (i.e., exposed to the human eye) to facilitate a procedure of biopsy or surgical excision of the area that has been highlighted by uptake of the compounds of the present disclosure. As the precise location and/or surface area of the tumor tissue are readily determined by the uptake of the compounds of the present disclosure, the methods employing the compounds of the present disclosure provide a valuable guide to the surgeon, who needs to "see" in real time the exact outlines, size, etc. of the mass to be resurrected as the surgery proceeds.

Thus, in specific embodiments, the present disclosure entails optical imaging of a biological tissue that expresses a folate receptor by contacting the tissue with a composition comprising compounds of the present disclosure (e.g., compounds of Formula I) and allowing time for the compound in the composition to distribute within the tissue and interact with the site of folate receptor. After a sufficient time for such interaction has passed, the tissue is illuminated with an excitation light to cause the compound in the composition to fluoresce. The fluorescence is then detected as and where such fluorescence is observed is an area that contains the folate receptor.

In like manner, the compounds of the present disclosure are used to identify a target cell type in a biological sample by contacting the biological sample with such compounds for a time and under conditions that allow for binding of the compound to at least one cell of the target cell type. The bound compound is then optically detected such that presence of fluorescence of the near infrared wavelength emanating from the bound, targeted compound of the present disclosure indicated that the target cell type is present in the biological sample. This method thus provides an image of the targeted cell type in the tissue being assessed. Most preferably, the targeted cell type is a tumor cell or a lymph node to which a tumor cell has spread.

These methods advantageously provide an improved method of performing image guided surgery on a subject as the administration of a composition comprising the compound of the disclosure under conditions and for a time sufficient for said compound to accumulate at a given surgical site will assist a surgeon in visualizing the tissue to be removed. Preferably the tissue is a tumor tissue and illuminating the compound that has been taken up by the tissue facilitates visualization of the tumor by the near infrared fluorescence of the compound using infrared light. With the aid of the visualization facilitated by the targeting of the compound of the disclosure to the tumors site, surgical resection of the areas that fluoresce upon excitation by infrared light allows an improved and accurate removal of even small tumors.

It should be understood that in any of the surgical methods of the disclosure the compounds of the present disclosure may be administered before the surgical incision takes place or even after the surgical cavity and site of the tumor has been revealed by the surgery.

If the putative diseased site is a natural body cavity or surgically produced interior site, an endoscopic device can be optionally used to deliver the excitation light to the site, to receive fluorescence emanating from the site within a body cavity, and to aid in formation of a direct image of the fluorescence from the diseased tissue. For example, a lens in the endoscopic device can be used to focus the detected fluorescence as an aid in formation of the image. As used herein, such endoscope-delivered fluorescence is said to be "directly viewed" by the practitioner and the tissue to which the targeting construct binds or in which it is taken up must be "in plain view" to the endoscope since the light used in the disclosure diagnostic procedure will not contain wavelengths of light that penetrate tissue, such as wavelengths in the near infrared range. Alternatively, the excitation light may be directed by any convenient means into a body cavity or surgical opening containing a targeting construct administered as described herein and the fluorescent image so produced can be directly visualized by the eye of the observer without aid from an endoscope. With or without aid from any type of endoscopic device, the fluorescent image produced by the disclosure method is such that it can be viewed without aid of an image processing device, such as a CCD camera, TV monitor, photon collecting device, and the like.

It is contemplated that the diagnostic or imaging methods of the present disclosure allow the surgeon/practitioner to contemporaneously see/view/visualize diseased or abnormal tissue through a surgical opening to facilitate a procedure of biopsy or surgical excision. As the location and/or surface area of the diseased tissue are readily determined by the diagnostic procedure of the disclosure employing the compounds described herein, the disclosure method is a valuable guide to the surgeon, who needs to know the exact outlines, size, etc. of the mass, for example, for resection as the surgery proceeds. In particular, it is noted that the compounds of the disclosure fluorescence in the near infrared range to a greater intensity than those previously described. As such, advantageously, it is contemplated that less of the compound will be needed to achieve diagnostic imaging. In addition, the compounds of the present disclosure penetrate deep into the tumor and hence the disclosure advantageously allows a greater accuracy that the tumor has been removed.

The present disclosure provides methods for utilizing a diagnostic procedure during surgery in a subject in need thereof by administering to the subject a composition comprising a compound of the present disclosure and irradiating an in vivo body part of the subject containing diseased tissue with light having at least one excitation wavelength in the range from about 600 nm to about 850 nm, directly viewing fluorescence emanating from a targeting construct administered to the subject that has specifically bound to and/or been taken up by the diseased tissue in the body part, wherein the targeting construct fluoresces in response to the at least one excitation wavelength, determining the location and/or surface area of the diseased tissue in the subject, and removing at least a portion of the tumor tissue.

In yet another embodiment, the present disclosure provides methods for in vivo diagnosis of tumor tissue in a subject in need thereof. In this embodiment, the disclosure method comprises contacting samples of tumor cells obtained from the subject in vitro with a plurality of detectably labeled compounds, each of which binds to or is selectively taken up by a distinct tumor type, determining which of the compounds is bound to or taken up by the sample tumor cells, administering a diagnostically effective amount of at least one biologically compatible fluorescing targeting construct containing a compound of the present disclosure that has been determined to bind to and/or be taken up by the sample tumor cells and a fluorophore responsive to at least one wavelength of light in the range from about 600 nm to about 850 nm, and diagnosing the location and/or surface area of the tumor tissue in the in vivo body part by directly viewing fluorescence emanating from the targeting construct bound or taken up in the tumor tissue upon irradiation thereof with light providing the at least one excitation wavelength for the fluorescent targeting construct.

In some embodiments, a single type of fluorescent moiety is relied upon for generating fluorescence emanating from the irradiated body part (i.e., from the fluorescent targeting construct that binds to or is taken up by diseased tissue) and subjecting the targeting construct with a source of light from the near infrared spectrum.

In other embodiments, it is contemplated that a plurality. (i.e., two, three, four, or more) targeting constructs are used to obtain a diagnostic image. Such additional targeting constructs may be additional compounds of the present disclosure distinct from the first such compound. Alternatively, the additional targeting constructs may comprise the dyes described herein but with the pteroyl moiety being replaced by a ligand for another receptor other than folate receptor. In still other embodiments, the additional targeting moieties may be other fluorescing targeting constructs (e.g., antibodies, or biologically active fragments thereof, having attached fluorophores) that bind to other receptors or antigens on the tumor or tissue (e.g., a site of atherosclerosis, infection, cardiovascular diseases, neurodegenerative diseases, immunologic diseases, autoimmune diseases, respiratory diseases, metabolic diseases, inherited diseases, infectious diseases, bone diseases, and environmental diseases or the like) to be imaged. Any additional targeting moiety that specifically targets the tumor or specific site on the tissue may be used provided that it is specific for the site to be monitored. The purpose of the additional fluorescing targeting construct is to increase the intensity of fluorescence at the site to be monitored thereby aiding in detection of diseased or abnormal tissue in the body part. For example, a given tumor may have numerous markers and in addition to the compounds of the present disclosure a cocktail of fluorescent moieties is provided which are specific for that given tumor such that the signal emanating from the tumor is generated by more than one compound or fluorescent moiety that has targeted and become localized to the tumor site of interest.

In practice, the skilled person would administer a compound of the present disclosure either alone or as part of a cocktail of targeting detectable moieties and allow these compounds and targeting moieties to bind to and/or be taken up by any targeting tissue that may be present at the site under investigation and then provide a supply of the light source. Typically, the compounds of the present disclosure and any additional targeting moieties will be administered prior to surgery for a time and in compositions that allow the fluorescent compounds of the present disclosure as well as any additional fluorescent constructs to be taken up by the target tissue.

Those of skill in the art will be able to devise combinations of successively administered fluorescing targeting constructs, each of which specifically binds to the target site. It is preferable that all of the fluorescing targeting constructs used in such cocktails to identify the target tissue comprise fluorophores that fluoresce within the same wavelength band or at the same wave length as does the compound of the present disclosure (e.g. a fluorescing sensitive to near infrared wavelength of light in the compounds of the present disclosure) to minimize the number of different light sources that need to be employed to excite simultaneous fluorescence from all of the different targeting constructs used in practice of the disclosure method. However, it is contemplated that the additional targeting moieties other than the compounds of the present disclosure may fluorescence in response to the irradiating light at a different color (i.e., has a different wavelength) than that from the florescent compounds of the present disclosure. The difference in the colors of the fluorescence emanating from the compounds of the present disclosure and those of the additional targeting compounds may aid the observer in determining the location and size of the diseased tissue. In some examples, it may be desirable to include fluorophores in targeting constructs targeted to target normal tissue and the compounds of the present disclosure to target diseased tissue such that the contrast between the diseased tissue and normal tissue is further enhanced to further aid the observer in determining the location and size of the target tissue. The use of such additional fluorophores and targeting agents in addition to the compounds of the present disclosure provides the advantage that any natural fluorescence emanating from normal tissue is obscured by the fluorescence emanating from fluorophore(s) in supplemental targeting constructs targeted to the normal tissue in the body part. The greater the difference in color between the fluorescence emanating from normal and target tissue, the easier it is for the observer to visualize the outlines and size of the target tissue. For instance, targeting a fluorescing targeting construct comprising a fluorophore producing infrared light from the compounds of the present disclosure to the target tissue (i.e., abnormal tissue) and a fluorophore producing green light to healthy tissue aids the observer in distinguishing the target tissue from the normal tissue. Those of skill in the art can readily select a combination of fluorophores that present a distinct visual color contrast.

The spectrum of light used in the practice of the disclosure method is selected to contain at least one wavelength that corresponds to the predominate excitation wavelength of the targeting construct, or of a biologically compatible fluorescing moiety contained within the targeting construct. Generally the excitation light used in practice of the disclosure method comprises at least one excitation wavelength of light in the near infrared wavelength range from about 600 nm to about 850 nm However, when a combination of targeting ligands that fluoresce at different wavelengths is used in practice of the disclosure, the spectrum of the excitation light must be broad enough to provide at least one excitation wavelength for each of the fluorophores used. For example, it is particularly beneficial when fluorophores of different colors are selected to distinguish normal from diseased tissue, that the excitation spectrum of the light(s) includes excitation wavelengths for the fluorophores targeted to normal and target tissue.

As noted herein the compounds of the present disclosure are specifically targeted to the folate receptor by way of pteroyl or folate ligand being part of the compounds of the present disclosure. In embodiments where an additional targeting moiety is used, the targeting construct of such an additional targeting moiety is selected to bind to and/or be taken up specifically by the target tissue of interest, for example to an antigen or other surface feature contained on or within a cell that characterizes a disease or abnormal state in the target tissue. As in other diagnostic assays, it is desirable for the targeting construct to bind to or be taken up by the target tissue selectively or to an antigen associated with the disease or abnormal state; however, targeting constructs containing ligand moieties that also bind to or are taken up by healthy tissue or cell structures can be used in the practice of the disclosure method so long as the concentration of the antigen in the target tissue or the affinity of the targeting construct for the target tissue is sufficiently greater than for healthy tissue in the field of vision so that a fluorescent image representing the target tissue can be clearly visualized as distinct from any fluorescence coming from healthy tissue or structures in the field of vision.

For example, colon cancer is often characterized by the presence of carcinoembryonic antigen (CEA), yet this antigen is also associated with certain tissues in healthy individuals. However, the concentration of CEA in cancerous colon tissue is often greater than is found in healthy tissue, so an anti-CEA antibody could be used as a ligand moiety in the practice of the disclosure. In another example, deoxyglucose is taken up and utilized by healthy tissue to varying degrees, yet its metabolism in healthy tissues, except for certain known organs, such as the heart, is substantially lower than in tumor. The known pattern of deoxyglucose consumption in the body can therefore be used to aid in determination of those areas wherein unexpectedly high uptake of deoxyglucose signals the presence of tumor cells.

The disease or abnormal state detected by the disclosure method can be any type characterized by the presence of a known target tissue for which a specific binding ligand is known. For example, various heart conditions are characterized by production of necrotic or ischemic tissue or production of artherosclerotic tissue for which specific binding ligands are known. As another illustrative example, breast cancer is characterized by the production of cancerous tissue identified by monoclonal antibodies to CA15-3, CA19-9, CEA, or HER2/neu. It is contemplated that the target tissue may be characterized by cells that produce either a surface antigen for which a binding ligand is known, or an intracellular marker (i.e. antigen), since many targeting constructs penetrate the cell membrane. Representative disease states that can be identified using the disclosure method include such various conditions as different types of tumors, bacterial, fungal and viral infections, and the like. As used herein "abnormal" tissue includes precancerous conditions, necrotic or ischemic tissue, and tissue associated with connective tissue diseases, and auto-immune disorders, and the like. Further, examples of the types of target tissue suitable for diagnosis or examination using the disclosure method include cardiac, breast, ovarian, uterine, lung, endothelial, vascular, gastrointestinal, colorectal, prostatic tissue, endocrine tissue, and the like, as well as combinations of any two or more thereof.

Simply by way of example, antigens for some common malignancies and the body locations in which they are commonly found are known to those of skill in the art, and targeting ligands, such as antibodies or for these antigens or indeed ligands where the antigens are receptors are known in the art. For example, CEA (carcinoembryoinc antigen) is commonly found in tumors from the colon, breast and lung; PSA (prostate specific antigen, or sometimes referred to as prostate specific membrane antigen (PSMA)) is specific for prostate cancer; CA-125 is commonly found in tumors of ovarian cancer origin, CA 15-3, CA19-9, MUC-1, Estrogen receptor, progesterone receptor and HER2/neu are commonly found in breast cancer tumors, alpha-feto protein is found in both testicular cancer and hepatic cancer tumors, beta-human chorionic gonadotropin is found testicular cancer and choriocarcinoma, both estrogen receptor and progesterone receptor also are found in uterine cancer tumors and epidermal growth factor receptor is commonly found in tumors from bladder cancer. Other tumor specific ligands and markers are well known to those of skill in the art. In preferred embodiments, the present disclosure employs folate or pteroyl moieties for targeting the folate receptor and PMSA target moieties for targeting the dyes to prostate cancer cells.

It is contemplated that any of these commonly known markers of tumors can be targeted either using the dyes described herein (by switching out the pteroyl moiety for a moiety that specifically targets these markers) or alternatively, these markers can be targeted in addition and in combination with the folate receptor that is being targeted using the compounds of the present disclosure. As discussed previously, it may be particularly advantageous to have targeting moieties to several different markers on a given tumor to serve as a diagnostic cocktail in which several markers are targeted to more brightly and clearly visualize the tumor.

In addition to chemical compounds, the targeting moieties in such cocktails may include a protein or polypeptide, such as an antibody, or biologically active fragment thereof, preferably a monoclonal antibody. The supplemental fluorescing targeting construct(s) used in practice of the disclosure method may also be or comprise polyclonal or monoclonal antibodies tagged with a fluorophore. The term "antibody" as used in this disclosure includes intact molecules as well as functional fragments thereof, such as Fab, F(ab')2, and Fv that are capable of binding the epitopic determinant. Methods of making these fragments are known in the art. (See for example, Harlow & Lane, Antibodies: A Laboratory Manual, Cold Spring Harbor Laboratory, New York, 1988, incorporated herein by reference). As used in this disclosure, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

In addition to antibodies, the cocktails may comprise compounds in which the ligand moiety attached to the fluorescent targeting construct is selected from among the many biologically compatible compounds that bind with specificity to receptors and/or are preferentially taken up by tumor cells, and can be used as the ligand moiety in the disclosure targeting constructs. Compounds that are preferentially "taken up" by tumor cells may enter the cells through surface or nuclear receptors (e.g., hormone receptors), pores, hydrophilic "windows" in the cell lipid bilayer, and the like.

Illustrative of this class of compounds to target tumors are somatostatin, somatostatin receptor-binding peptides, deoxyglucose, methionine, and the like. Particularly useful somatostatin receptor-binding peptides are a long-acting, octapeptide analog of somatostatin, known as octreotide (D-phenylalanyl-L-cysteinyl-L-phenylala-nyl-D-tryptophyl-L-lysyl-L-threonyl-N-[2-hydroxy-1-(hydroxymethyl) propyl]-L-cysteinamide cyclic (2→7)-disulfide), lanreotide, an oral formulation of octreotide, P829, P587, and the like. Somatostatin-binding peptides are disclosed in U.S. Pat. No. 5,871,711, and methods for linking such peptides covalently to a radioisotope through their carboxyl terminal amino acid under reducing conditions are disclosed in U.S. Pat. No. 5,843,401, which are both incorporated herein by reference in their entireties. One of skill in the art can readily adapt such teachings for the preparation of fluorescence-sensitive somatostatin receptor-binding peptides by substituting the fluorescing moieties of this disclosure in the place of a radioisotope.

Somatostatin and somatostatin receptor-binding peptides are particularly effective for use as the tumor-targeting ligand moiety in the targeting construct when the disease state is a neuroendocrine or endocrine tumor. Examples of neuroendocrine tumors that can be diagnosed using the disclosure method include adenomas (GH-producing and TSH-producing), islet cell tumors, carcinoids, undifferentiated neuroendocrine carcinomas, small cell and non-small cell lung cancer, neuroendocrine and/or intermediate cell carcinomas, neuroendocrine tumors of ovary, cervix, endometrium, breast, kidney, larynx, paranasal sinuses, and salivary glands, meningiomas, well differentiated glia-derived tumors, pheochromocytomas, neuroblastomas, ganglioneuro(blasto)mas, paragangliomas, papillary, follicular and medullary carcinomas in thyroid cells, Merkel cell carcinomas, and melanomas, as well as granulomas and lymphomas. These tumor cells are known to have somatostatin receptors and can be targeted using somatostatin or somatostatin receptor binding peptides as the tumor-targeting ligand in the disclosure fluorescent targeting construct.

Vasointestinal peptide (VIP), which is used in VIP receptor scintigraphy (I. Virgolini, Eur J. Clin. Invest. 27(10): 793-800, 1997, is also useful in the disclosure method for diagnosis of small primary adenocarcinomas, liver metastases and certain endocrine tumors of the gastrointestinal tract.

Another molecule illustrative of the tumor-targeting ligands that are preferentially taken up by tumors is deoxyglucose, which is known to be preferentially taken up in a variety of different types of tumors. Illustrative of the types of tumors that can be detected using deoxyglucose as the tumor-targeting ligand include melanoma, colorectal and pancreatic tumors, lymphoma (both HD and NHL), head and neck tumors, myeloma, cancers of ovary, cancer, breast, and brain (high grade and pituitary adenomas), sarcomas (grade dependent), hepatoma, testicular cancer, thyroid (grade dependent) small cell lung cancer, bladder and uterine cancer, and the like.

Yet other tumor-targeting compounds that can be used in cocktails of the present disclosure include 1-amino-cyclobutane-1-carboxylic acid and L-methionine. L-methionine is an essential amino acid that is necessary for protein synthesis. It is known that malignant cells have altered methionine metabolism and require an external source of methionine.

Additional examples of biologically compatible tumor-targeting compounds that bind with specificity to tumor receptors and/or are preferentially taken up by tumor cells include mammalian hormones, particularly sex hormones, neurotransmitters, and compounds expressed by tumor cells to communicate with each other that are preferentially taken up by tumor cells, such as novel secreted protein constructs arising from chromosomal aberrations, such as transfers or inversions within the clone.

Hormones, including sex hormones, cell growth hormones, cytokines, endocrine hormones, erythropoietin, and the like also serve well as tumor targeting moieties. As is known in the art, a number of tumor types express receptors for hormones, for example, estrogen, progesterone, androgens, such as testosterone, and the like. Such hormones are preferentially taken up by tumor cells, for example, via specific receptors.

The targeting constructs and supplemental targeting constructs used in practice of the disclosure method can be administered by any route known to those of skill in the art, such as topically, intraarticularly, intracisternally, intraocularly, intraventricularly, intrathecally, intravenously, intramuscularly, intraperitoneally, Experimental Section:
  Materials:
    $N^{10}$-Trifluroacetylpteroic acid [Pte-$N^{10}$-(TFA)-OH] (Irvine Chemistry Lab, Anaheim, Calif.). O-t-Butyl-L-tyrosine t-butyl ester hydrochloride and O-(7-azabenzo-triazol-1-yl)-N,N,N',N'-tetramethyluronium hexafluorophosphate (HATU) (Chem-Impex Int., Chicago, Ill.). All other chemicals, cell culture materials, and animal supplies were obtained from major suppliers.
  General Methods:
    Moisture and oxygen sensitive reactions were carried out under an argon atmosphere. Solid phase peptide synthesis (SPPS) was performed using a standard peptide synthesis apparatus (Chemglass, Vineland, N.J.). Flash chromatography was conducted with silica gel as the solid phase, and TLC was performed on silica gel TLC plates (60 f254, 5×10 cm) and visualized under UV light. All peptides and peptide conjugates were purified by preparative reverse phase (RP)-HPLC (Waters, xTerra C18 10 μm; 19×250 mm) and analyzed UPLC (Acquity, BEH C18 1.7 μm; 2.1×50 mm) using solvent A=10 mM Ammonium acetate ($NH_4OAc$; pH=7.0) and solvent B=Acetonitrile ($CH_3CN$). $^1H$ and $^{13}C$ spectra were acquired with a Bruker 500 MHz and 125 MHz NMR spectrometer equipped with a TXI cryoprobe. Samples were run in 5 mm NMR tubes using DMSO-d6, or DMSO-$d_6$/$D_2O$. Pre-saturation was used to reduce the intensity of the residual $H_2O$ peak. All $^1H$ signals are recorded in ppm with reference to residual trichloromethane (also known as chloroform or CHCl3) (7.27 ppm) or dimethyl sulfoxide (DMSO) (2.50 ppm), and data are reported as s=singlet, d=doublet, t=triplet, q=quartet, and m=multiplet or unresolved, b=broad, with coupling constants in Hz.

LC/MS analyses were obtained using a Waters micromass ZQ 4000 mass spectrometer coupled with a UV diode array detector. High resolution mass spectrometric results were obtained by matrix-assisted laser desorption ionization (MALDI) mass using an Applied Biosystems (Framingham, Mass.) Voyager DE PRO mass spectrometer. This instrument utilizes a nitrogen laser (337 nm UV laser) for ionization with a time-of-flight mass analyzer. The matrix used for these samples was alpha-cyano-4-hydroxy cinnamic acid and the peptide LHRH was used as internal standard.

KB cells [a derivative of HeLa cells (a human cervical cancer cell line)], IGROV cells (a human ovarian cancer cell line), SKOV3 cells (a human ovarian cancer cell line), OVCAR3 cells (a human ovarian cancer cell line), HCC827 (a human non-small cell lung cancer cell line), MDA-MB231 (a human breast cancer cell line), M109 (murine lung cancer cell line), and A549 cells (a alveolar basal epithelial carcinoma cell line) were obtained from American Type Culture Collection (ATCC) (Rockville, Md.) and grown as a monolayer and L1210 (a human leukemia cell line) grown as suspension using folate free or normal 1640 RPMI-1640 medium (Gibco, NY) containing 10% heat-inactivated fetal bovine serum (Atlanta Biological, GA) and 1% penicillin streptomycin (Gibco, NY) in a 5% carbon dioxide: 95% air-humidified atmosphere at 37° C. for at least six passages before they were used for the assays.

Athymic female nude (nu/nu) and Balb/C mice (5 weeks old, 18-20 g) were purchased from Harlan (Indianapolis, Ind.) and maintained on gamma-irradiated folate-deficient special diet (Teklad, WI) for at least 2 weeks before start of the study. Animals were housed with five mice per cage (5/cage) in a barrier, pathogen-free cloaked rack. Autoclaved tap water and food were given as needed. The animals were housed in a sterile environment on a standard 12 hour light-dark cycle for the duration of the study. Mice were identified individually by ear punch.

In Vitro Binding:
  Column 88, lines 10-31 of U.S. Pat. No. 9,061,057 are expressly incorporated by reference.
  Flow Cytometry:
    KB (a human cervical cancer cell line), IGROV (a human ovarian cancer cell line), SKOV3 (a human ovarian cancer cell line), OVCAR3 (a human ovarian cancer cell line), HCC827 (a human lung cancer cell line), MDA-MB231 (a human triple negative breast cancer cell line), M109 (a murine lung cancer cell line), A549 (a human lung cancer cell line), L1210 (a murine leukemia cancer cell line) cells were seeded into a T75 flask and allowed to form a monolayer over 24 hours and L1210 cells were grown in suspension. After trypsin digestion, release cells were transferred into centrifuge tubes (1×10⁶ cells/tube) and centrifuged. The medium was replaced with fresh medium containing the compound of interest (100 nM) in the presence or absence of 100-fold excess FA and incubated for 1 hour at 37° C. After rinsing twice with 1 mL of fresh medium (2×1.0 mL) and once with 1 mL of PBS (1×1.0 mL), cells were resuspended in 1 mL of PBS and cell bound fluorescence was analyzed (100,000 cells/sample) using a flow cytometer (Cytomics F500, Beckman Coulter). Untreated cells in PBS served as a negative control.

Confocal Microscopy:

KB, IGROV, SKOV3, MDA-MB231, or A549 cells (50,000 cells/well in 1 mL) were seeded into poly-D-lysine microwell Petri dishes and allowed cells to form monolayers over 12 hours. Spent medium was replaced with fresh medium containing 100 nM of the compound of interest (100 nM) in the presence or absence of 100-fold excess FA and cells were incubated for 1 hour at 37° C. After rinsing twice with 1.0 mL fresh medium (2×1.0 mL) and once with 1.0 mL PBS (1×1.0 mL), confocal images were acquired using a confocal microscopy (FV 1000, Olympus).

Whole Body Imaging:

(a) Xenograft Model:

Seven-week-old female nu/nu mice were inoculated subcutaneously with KB (1.0×10⁶/mouse in RPMI1640 medium), IGROV (5.0×10⁶/mouse in 50% high concentrated matrigel +RPMI1640 medium), SKOV3 (5.0×10⁶/mouse in RPMI1640 medium), OVCAR3 (5.0×10⁶/mouse in RPMI1640 medium), MDA-MB231 (1.0×10⁶/mouse in RPMI1640 medium), M109 (1.0×10⁶/mouse in RPMI1640 medium) or A549 cells (2.0×10⁶/mouse in RPMI1640 medium) on the shoulder. Growth of the tumors was measured in perpendicular directions every 2 days using a caliper (body weights were monitored on the same schedule), and the volumes of the tumors were calculated as $0.5 \times L \times W^2$ (L=longest axis and W=axis perpendicular to L in millimeters). Once tumors reached approximately 300-400 mm³ in volume, animals (3-5 mice/group) were intravenously injected with the compound of interest in PBS (for dose escalation in KB tumor model: 0.3-90 nmol, for time dependent in KB tumor model: 2 or 10 nmol, and for general whole body imaging and biodistribution for all tumor models: 2 nmol, in 100 µL in PBS per mouse). For whole body imaging and biodistribution studies, animals were euthanized 2 hours after administration of the compound of interest by $CO_2$ asphyxiation. For time dependent studies, animals were imaged under anesthesia using isoflurane. Whole body imaging (intact tumor) experiments was then performed using a Caliper IVIS Lumina II Imaging Station with Living Image 4.0 software (PerkinElmer Inc, MA).

(b) Orthotopic Models:

Ovarian cancer was developed through surgical implantation of ovarian cancer cell lines near the ovarian bursa of the mouse. Seven-week-old female athymic nude mice were given 1-5% isoflurane for anesthesia and subcutaneous injection of 5 mg/kg meloxicam preoperatively for analgesia. The mice were placed dorsal side up and washed above the right ovary (just lateral to the epaxial muscles and ~1.15 cm caudal to the rib cage) with a chlorhexidine scrub to ensure a sterile area for incision. After an insertion was made using scalpel through the skin, the peritoneal lining was lifted to make a small incision using a scissor and widened using a forceps. The ovarian fat pad was carefully lifted out and placed on a wetted gauze pad adjacent to the incision. Ovarian cancer cells (50,000 cells in 5 µL) were injected between the bursa and the ovary using a 30 gage needle. After placing the ovarian fat pad back into the body cavity, the body wall was closed using 3-0 or 4-0 vicryl and the skin was closed using staples.

Breast cancer was developed by implanting breast cancer cells in the memory fat pad of the mouse.

(c) Metastatic Models:

One million (1×10⁶) of either L1210A or MDA-MB231 cancer cells per mouse (cancer cells/mouse) were administered via tail vein injection into the mice. Tumor growth was monitored every other day using a Caliper IVIS Lumina II Imaging Station with Living Image 4.0 software (PerkinElmer Inc.).

Tissue Distribution:

Following whole body imaging, animals were dissected and selected tissues (heart, lung, liver, spleen, kidneys, stomach, small intestine, large intestine, muscle, skin, and tumor) were analyzed for fluorescence activity using IVIS imager using same settings as in whole body imaging.

Example 1

Design and Synthesis

Scheme 1:

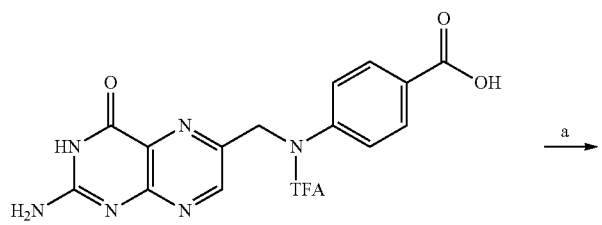

1

-continued

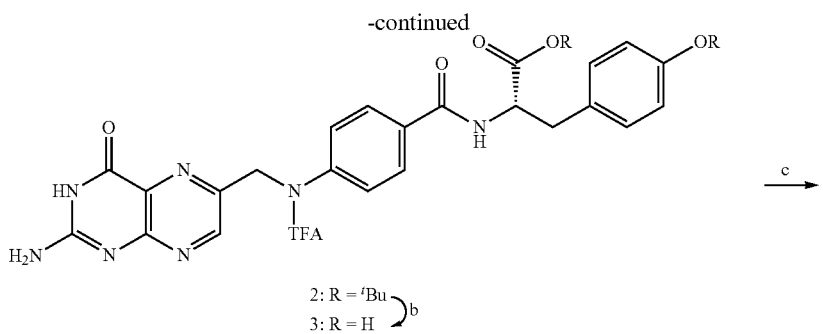

2: R = ⁱBu  ⎫
3: R = H   ⎬ b

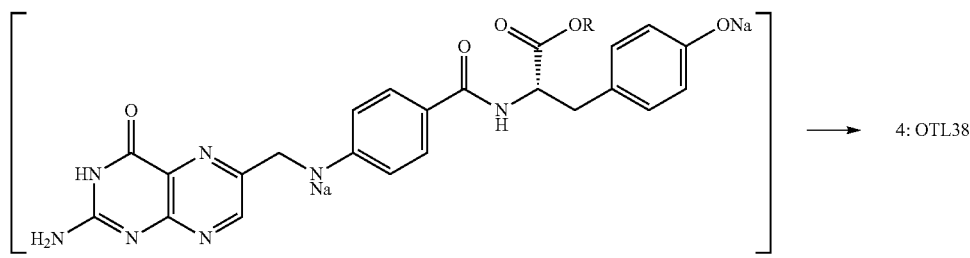

4: OTL38

Reagents and conditions for synthesis of OTL 38: (a) (i) HATU, H₂N—Tyr(OᵗBu)—OᵗBu•HCl, DMF, (ii) DIPEA, 23° C., 2 h; (b) TFA:TIPS:H₂O (95:2.5:2.5), 23° C., 1 h; (c) (i) H₂O/NaOH (pH = 9.5), (ii) S0456, H2O, 23° C., (iii) 90° C., 45 min.

A synthesis of compound 4 (OTL38) is shown in Scheme 1. $N^{10}$-Trifluroacetylpteroic acid was first reacted with tert-butyl protected tyrosine in the presence of HATU, an acid activating group, to generate compound 2 in quantitative yield. The compound 2 was precipitated under mild acidic conditions and then treated with a cocktail of trifluroacetic acid, tri-isopropylsilane, and water to de-protect tertiary butyl groups from the acid and hydroxyl group. After precipitating the compound 3 in ether, it was dissolved in water at pH 9.5 to produce compound 4.

Example 2

Comparison of Chemical and Optical Properties of Compound 4 with Commercially Available NIR Fluorophores Example 3

In Vitro Binding Affinity and Specificity in Human Cervical Tumor Xenograft Model Overexpression of FR-α in KB cells (a derivative of HeLa cell line and HeLa cells are human cervical cancer cell line) is well established in the literature. Therefore, all the initial optimizations were done using KB cells. Optimized conditions were used in the ovarian cancer xenografts and orthotopic modes.

Example 6 (Column 71, line 44 to Column 72, line 35) of U.S. Pat. No. 9,061,057 is expressly incorporated by reference with compound 6 described in the '057 patent as OTL-0038.

TABLE 1

Comparison of chemical and optical properties of NIR dyes

| Property | CW800 | ZW80o | LS288 | Kodak | ICG | OTL38 | CY7 | Cy7.5 | Alx750 | DyL750 |
|---|---|---|---|---|---|---|---|---|---|---|
| MW (Da) | 1091 | 1149 | 973 | 1117 | 775 | 1326 | 549.8 | 649.9 | ~1300 | 1092 |
| E ($M^{-1}$ $cm^{-1}$) | 237000 | 249000 | 122000 | 224000 | 121000 | 272000 | 240600 | 223000 | 290000 | 220000 |
| λem (nm) | 786 | 772 | 761 | 802 | 807 | 776 | 750 | 788 | 753 | 754 |
| λex (nm) | 800 | 788 | 778 | 818 | 822 | 796 | 773 | 808 | 782 | 776 |
| Stokes Shift (nm) | 14 | 16 | 17 | 16 | 15 | 20 | 23 | 20 | 29 | 22 |
| Q (%) | 14.2 | 15.1 | 11.2 | 12.5 | 9.3 | 15.6 | | | | |
| Cost/g ($) | 30,000 | 50,000 | | | 1,500 | <500 | 12,000 | 12,000 | 50,000 | 50,000 |

Example 4

Binding and Internalization of Compound 4 to Human Cervical Cancer and Triple Negative Breast Cancer Cells by Confocal Microscopy The binding and internalization of OTL38 is illustrated in FIGS. 3A, 4B, 4D, and 4E. KB, MDA-MB231 and SKOV3 cells each independently express FR-alpha while A549 cells do not.

Example 5

In Vivo Efficacy of OTL38 in a Human Cervical Cancer Xenograft Model that Express High Levels of FR-α

Figure 4A:
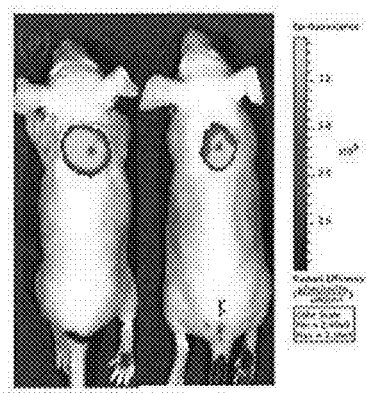
FIG. 4A depicts an overlay of whole body fluorescence image over white light image (after adjusting the threshold). Mice were injected with 10 nmol of OTL38, euthanized and imaged with IVIS imager 2 hours post injection. Exposure time=1 s; Excitation: 745 nm. Emission: ICG (indocyanine green). Mice were bearing human cervical tumor xenografts.
Figure 4B:
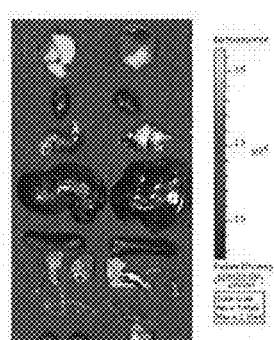
FIG. 4B depicts tissue biodistribution analysis using fluorescence imaging of two mice from FIG. 4A.
Figure 4C:
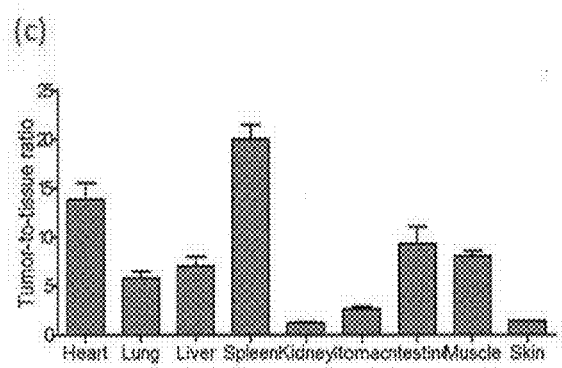
FIG. 4C depicts tumor-to-tissue ratio from tissue biodistribution data of human cervical tumor xenograft model of FIG. 4A.

Analysis of whole body imaging demonstrated that OTL38 accumulated predominantly in the FR positive KB tumors, with no substantial fluorescence activity in the other tissues (FIG. 4A). Analysis of tissue biodistribution was performed on the same animals that were subjected to whole body imaging by euthanizing each mouse, removing their organs and imaging using IVIS imager. The highest fluorescence intensity was observed in FR-positive tumors with no accumulation in the other tissues except the kidneys and skin (FIG. 4B). All FR-negative tissues displayed very low uptake levels of OTL38 resulting in excellent tumor-to-tissue ratios except the skin (FIG. 4C). Uptake of OTL38 in the kidneys was anticipated, since the apical membrane of the proximal tubule of the kidney has been known to express high levels of FR. Moreover, it's possible that the compound 4 is excreted through the kidneys due to their low molecular weights and half-life (most of the folate conjugates have <30 min half-life). Fluorescence in the skin can be due to reflection of the light from the skin and/or skin tissue of the nude mice may have higher level of immune cells such as monocytes, macrophages, etc. These immune cells express FR beta and OTL38 binds to FR-alpha and beta with same affinity. On the other hand, the dye component of OTL38 may non-specifically bind to the nude mice skin tissue with slow clearance at 2 h time point.

Figures 5A, 5B, 5C:
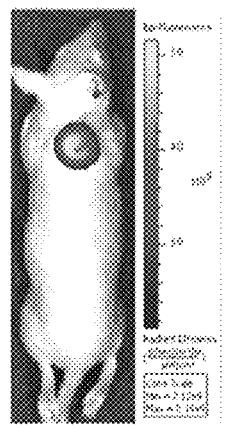
FIG. 5A depicts an overlay of whole body fluorescence image over white light image after adjusting the threshold. The mouse was injected with 10 nmol of OTL38, euthanized and imaged with IVIS imager 24 hours post injection and analyzed using ImageJ analysis software. Exposure time=1 s; Excitation: 745 nm. Emission: ICG (indocyanine green). Mouse was bearing human cervical tumor xenografts.
FIG. 5B depicts a gray scale fluorescence of the mouse of FIG. 6A.
FIG. 5C depicts a plot of gray value Vs distance (c) across the line shown in FIG. 5B.
Figure 5D:
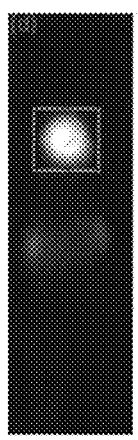
Figure 5E:
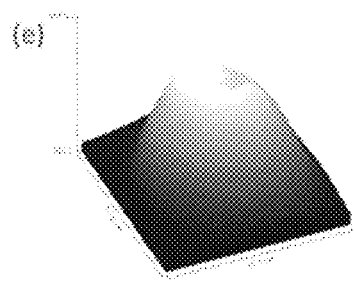
FIG. 5E depicts a 3D plot of gray value Vs within the box shown in FIG. 5D for a mouse bearing human cervical tumor xenografts.

Following 24 hours post injection of OTL38, tumor-to-skin ratio of a KB tumor bearing mouse was further evaluated using ImageJ analysis (free software that can be downloaded from NIH website) as illustrated in FIGS. 5A-5E. The whole body image of the mouse was acquired as fluorescence in a yellow-red scale (FIG. 5A) and a gray scale (FIGS. 5B and D). A line (FIG. 5B) or a box (FIG. 5D) was drawn across the skin and tumor, and the tumor-to-skin ratio was analyzed using a plot of the fluorescence gray value vs. distance. As shown in the FIGS. 5C and E, fluorescence intensity in the skin is minimal at the 24 h time point compared to fluorescence intensity in the tumor, indicating that OTL38 has minor nonspecific skin tissue uptake (most probably either OTL38 binds to FR beta on the immune cells in the skin and/or there is non-specific binding of the dye component of the OTL38) that clears within 24 h. More importantly, we assume that the fluorescence in the skin, even if there is minor uptake, this should not cause any interference during an image guided open surgery for ovarian cancer.

Example 6

Optimal Dose Determination in a Human Cervical Cancer Xenograft Model that Express High Levels of FR-α

In order to determine the optimal dose of OTL38 that has higher tumor uptake and higher tumor-to-background ratio, a dose dependent study was conducted by injecting increasing concentrations of OTL38 (0.3, 1.3, 10, 20, 30, 60, and 90 nmol) to mice bearing KB tumor xenografts. Animals were sacrificed, the tissues were harvested, and they were imaged using the IVIS imager. As shown in the Table 1 and FIGS. 6(A-H), all the doses had higher tumor uptake in the folate receptor-positive tumors except 0.3 nmol dose. On the other hand, higher kidney uptake was also observed for dose range 0.3-10 nmol and less kidney uptake (relative to tumor uptake) was observed for dose range 30-90 nmol. Moreover, higher non-specific uptake in healthy tissues was observed at 60 and 90 nmol doses. OTL38 showed lower uptake in FR-positive tumors (weak fluorescence intensity) at 0.3 nmol dose may be due to incomplete saturation of FR on the tumor cells.

Figure 6A:
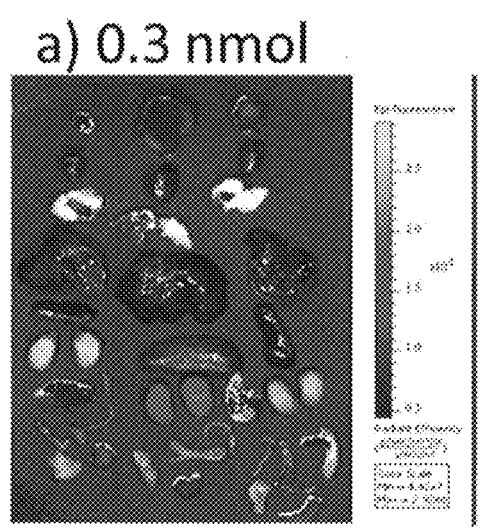
FIG. 6A depicts a tissue biodistribution analysis using fluorescence imaging at 0.3 nmol dose of OTL38. Human cervical tumor xenografts bearing mice were injected with 2 nmol of OTL38, euthanized and imaged with IVIS imager 2 hours post injection. Exposure time=1 s; Excitation: 745 nm. Emission: ICG (indocyanine green).
Figure 6B:
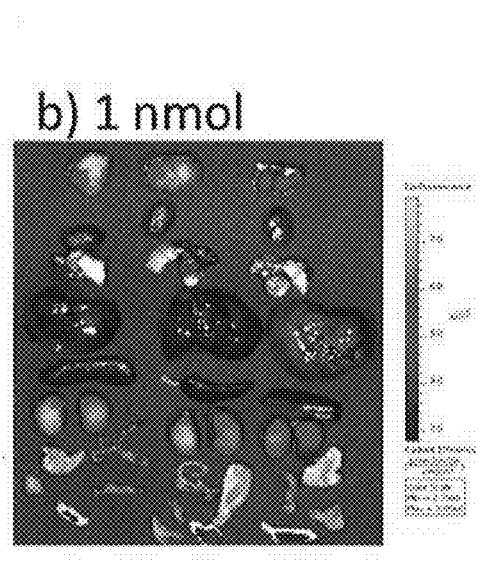
FIG. 6B depicts a tissue biodistribution analysis using fluorescence imaging at 1.0 nmol dose of OTL38.
Figure 6C:
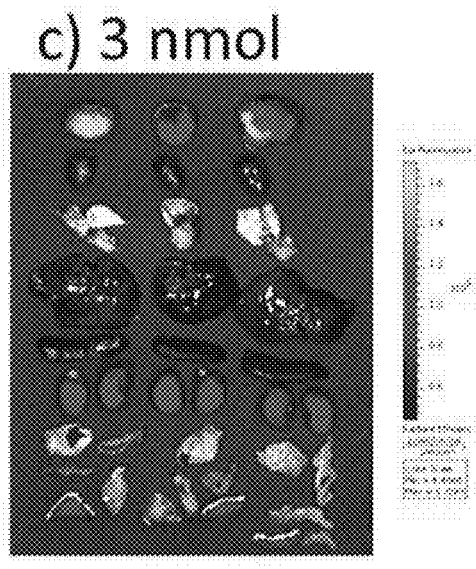
FIG. 6C depicts a tissue biodistribution analysis using fluorescence imaging at 3.0 nmol dose of OTL38.
Figure 6D:
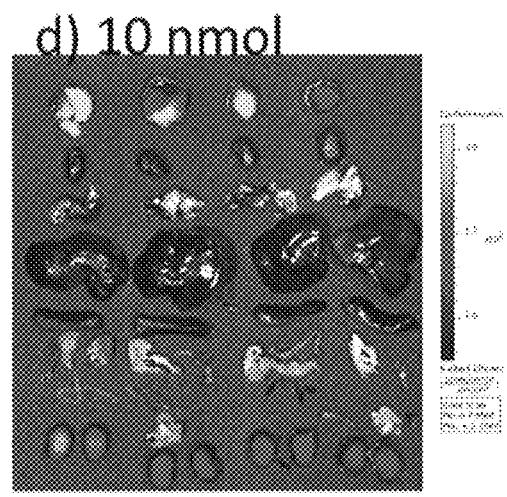
FIG. 6D depicts a tissue biodistribution analysis using fluorescence imaging at 10 nmol dose of OTL38.
Figure 6E:
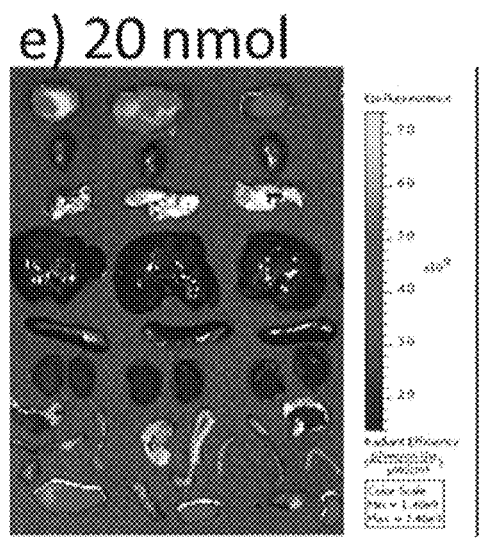
FIG. 6E depicts a tissue biodistribution analysis using fluorescence imaging at 20 nmol dose of OTL38.
Figure 6F:
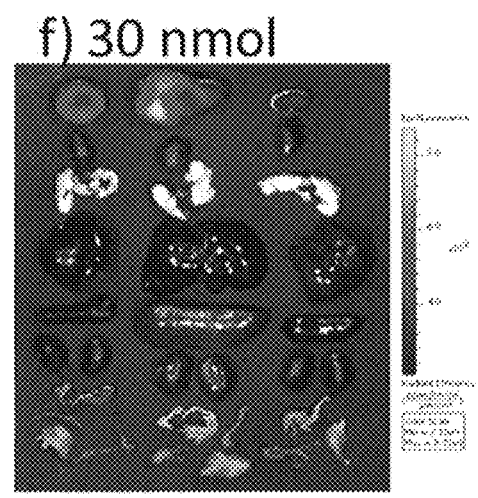
FIG. 6F depicts a tissue biodistribution analysis using fluorescence imaging at 30 nmol dose of OTL38.
Figure 6G:
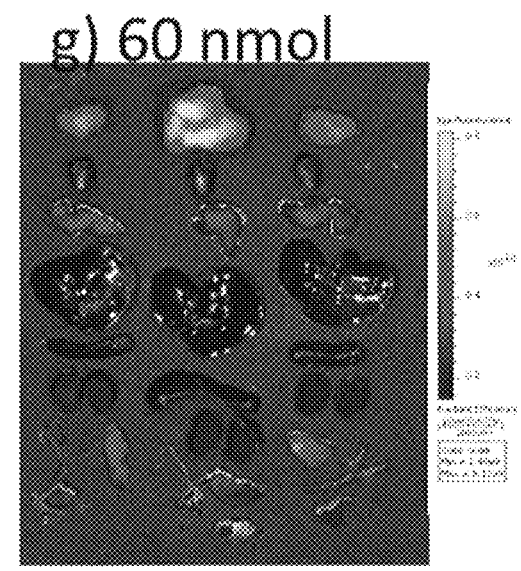
FIG. 6G depicts a tissue biodistribution analysis using fluorescence imaging at 60 nmol dose of OTL38.
Figure 6H:
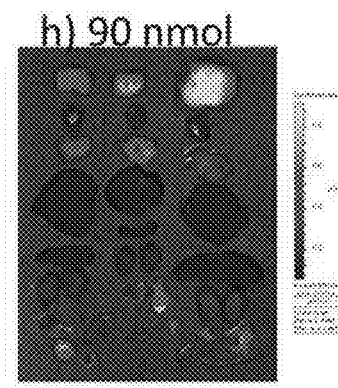
FIG. 6H depicts a tissue biodistribution analysis using fluorescence imaging at 90 nmol dose of OTL38.
Figure 6I:
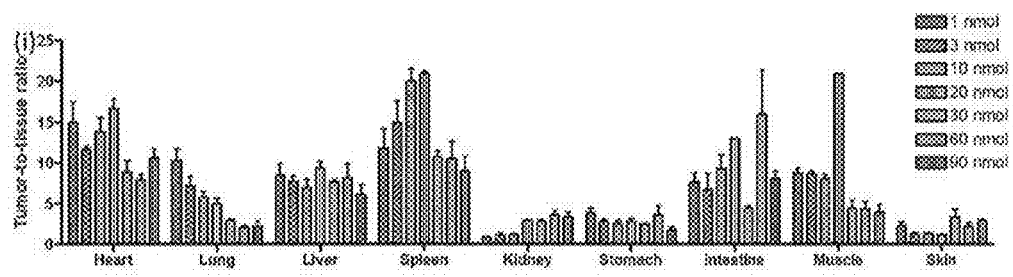
FIG. 6I depict plots of a tissue biodistribution analysis using fluorescence imaging at FIGS. 6A-HC dose levels of OTL38.

Dose range between 1.0-30.0 nmol showed very good tumor uptake and excellent tumor-to-normal tissue ratio (FIG. 6I. Higher than 30 nmol dose kidney uptake may be due to the clearance of the probe through the kidneys and expression of folate receptor on kidneys.

Dose levels 60.0 nmol and 90.0 nmol show higher non-specific uptake. However, these dose levels still have high tumor uptake and less kidney uptake, including 30 nmol dose. Less kidney uptake may be due to the alternative clearance of the probe through liver and gut. Therefore, OTL38 may be forming aggregates at these higher concentrations.

Therefore, we concluded that about 1.0-about 3.0 nmol are the lowest doses to administer to obtain good tumor-to-background ratio while maintaining the non-invasive aspect for tumor imaging (FIG. 6). Moreover, 30 nmol may be the highest dose that could administer to obtain best tumor-to-background ratio. Therefore, we decided to use 2 nmol of OTL38 for the rest of the animal studies.

Example 7

Efficacy of in a Human Cervical Cancer Xenograft Model at Optimize Dose that Express High Levels of FR-α

Figure 7A:
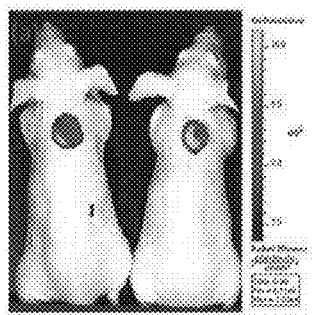
FIG. 7A depicts an overlay of whole body fluorescence image over white light images (after adjusting the threshold). Human cervical tumor xenograft bearing mice injected with 2 nmol of compound 4 and image with IVIS imager at 2 hours post injection. Exposure time=1 s; Excitation: 745 nm. Emission: ICG (indocyanine green).
Figure 7B:
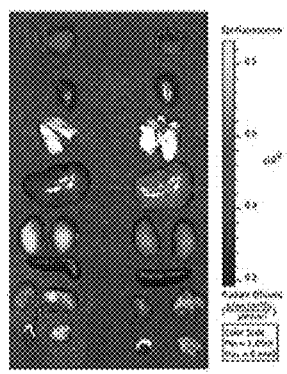
FIG. 7B depicts a tissue biodistribution analysis using fluorescence imaging of two mice of FIG. 7A.
Figure 7C:
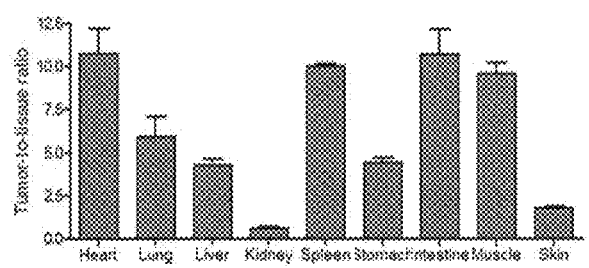
FIG. 7C depicts tumor-to-tissue ratio from tissue biodistribution data of a human cervical tumor xenograft bearing mice of FIG. 7A.

As shown in FIGS. 7A-7C, OTL38 demonstrated an excellent whole body imaging (FIG. 7A), tissue biodistribution (FIG. 7B), and tumor-to-tissue (FIG. 7C) at 2 nmol dose at 2 h post injection.

Example 8

Time to Determine Optimal Image in a Human Cervical Cancer Xenograft Model

In effort to determine the optimal time to image with higher tumor uptake and higher tumor-to-background ratio, time dependent study was conducted. By administering 10 nmol of OTL38 via tail vein and live imaging was conducted using IVIS imager from 15 min to 48 h post injection.

Figure 8:
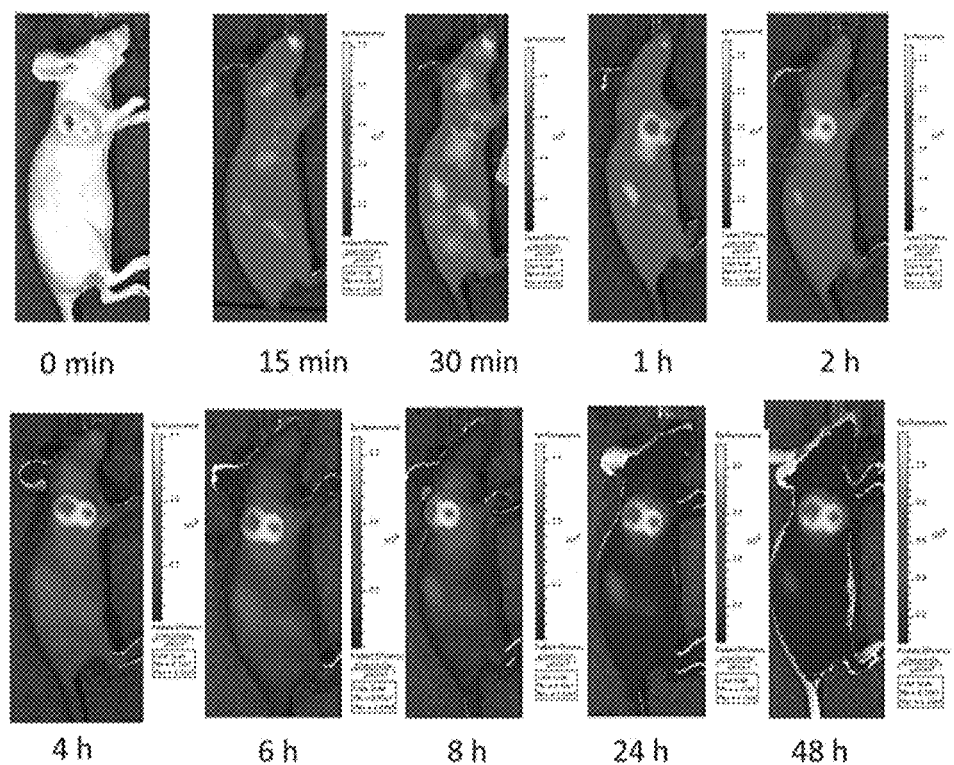
FIG. 8 depicts an overlay of time dependent whole body fluorescence image over white light images before adjusting the threshold. Human cervical tumor bearing mice were injected with 10 nmol of OTL38 and image with IVIS imager at different time intervals. Exposure time=1 s; Excitation: 745 nm. Emission: ICG (indocyanine green).

The time dependent study demonstrated that OTL3 accumulated in the FR positive tumor and kidneys within 1 hour and saturated FR [$1.2$-$1.5 \times 10^9$ (p/sec/cm$^2$/sr)/($\mu$W/cm$^2$)] within 2-4 hours. FIG. 8 also shows that OTL38 starts clearing from the skin at 2 hour time point and minimal fluorescence was observed at 24-48 hour time points. However, fluorescence in tumor remains high even at 48 hour time point.

Example 9

In Vivo Efficacy of OTL38 in a Human Ovarian Cancer (IGROV, a Human Ovarian Cancer Cell Line) Model that Express Moderate Levels of FR-α

(a) Xenograft Tumor Model

Figure 9A:
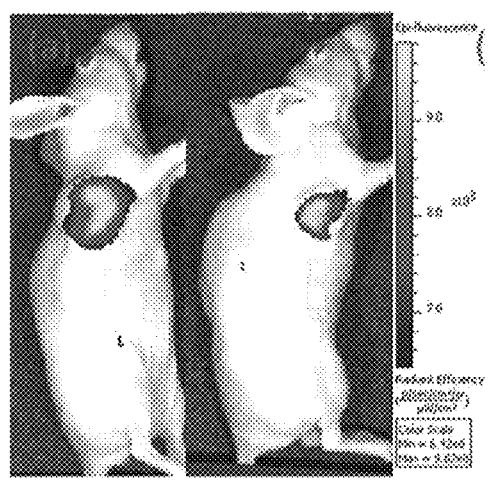
FIG. 9A depicts an overlay of whole body fluorescence image over white light images (after adjusting the threshold). Human ovarian (IGROV) xenograft tumor bearing mice injected with 2 nmol of OTL38 and image with IVIS imager at 2 hours post injection. Exposure time=1 s; Excitation: 745 nm. Emission: ICG (indocyanine green).
Figure 9B:
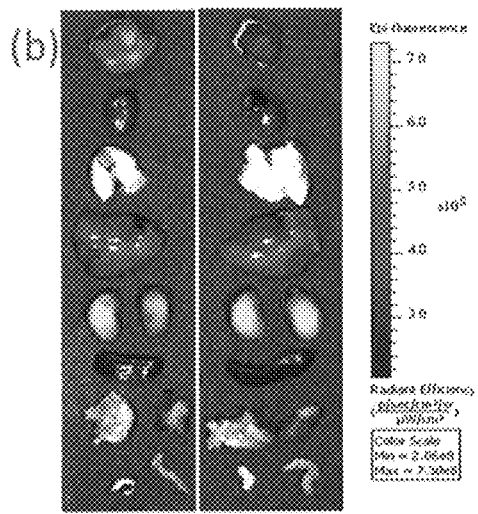
FIG. 9B depicts a tissue biodistribution analysis using fluorescence imaging of mice of FIG. 9A.
Figure 9C:
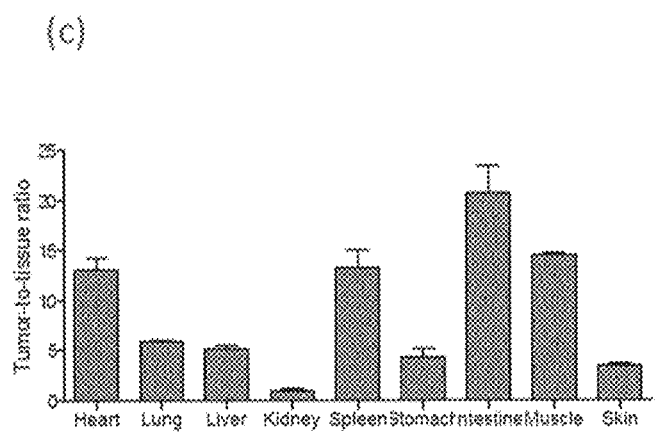
FIG. 9C depicts a tumor-to-tissue ratio from tissue biodistribution data of mice of FIG. 9A.

As seen in the FIG. 9A, OTL38 accumulated mainly in the FR-positive IGROV tumor xenografts, with no substantial fluorescence activity in the other tissues. To quantitate in vivo specificity of OTL38 to ovarian cancer, ex-vivo tissue biodistribution study was performed on the same animals that were subjected to whole body imaging. The highest fluorescence intensities were observed in FR-positive tumors and kidneys (FIG. 9B). All the other normal tissues displayed minimal levels or no uptake, resulting in excellent tumor-to-normal tissue ratios (FIG. 9C) especially given IGROV cells express moderate levels of FR-α.

(b) Ovarian Cancer Orthotopic Model

Figure 10A:
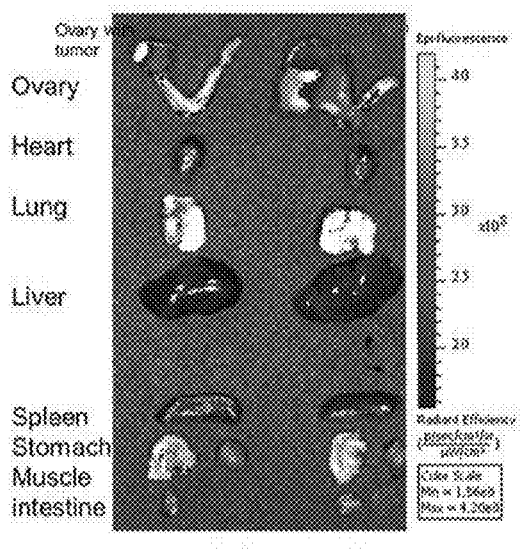
FIG. 10A depicts a tissue biodistribution analysis as an overlay of fluorescence image over white light image (after adjusting the threshold) of selected tissues of a human ovarian (IGROV) orthotropic tumor mouse injected with 2 nmol of OTL38 and imaged with IVIS imager at 2 hours post injection. Exposure time=1 s; Excitation: 745 nm. Emission: ICG (indocyanine green).
Figure 10B:
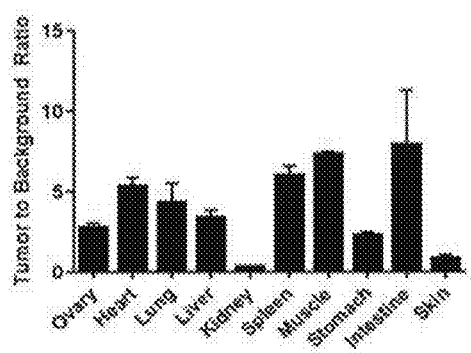
FIG. 10B depicts a tissue biodistribution analysis as tumor-to-tissue ratio from mouse of FIG. 10A.

As seen in FIG. 10A, OTL38 accumulated mainly in the FR-positive IGROV orthotopic ovary tumor and there was no substantial fluorescence activity in the healthy ovary or the other tissues except kidneys resulting in excellent tumor-to-normal tissue ratios (FIG. 10B). Note: Kidneys were removed from the biodistribution images.

Example 10

In Vivo Efficacy of OTL38 in a Human Ovarian Cancer (SKOV3, a Human Ovarian Cancer Cell Line) Model that Express Low Levels of FR-α

(a) Xenograft Tumor Model

Figure 11A:
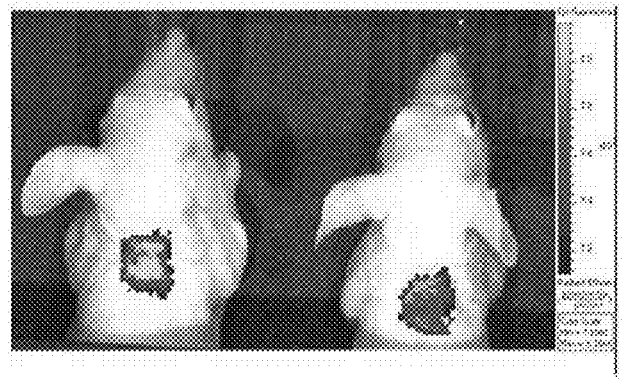
FIG. 11A depicts an overlay of half body fluorescence image over white light image (after adjusting the threshold). Tissue biodistribution data of a human ovarian (SKOV3) tumor bearing mice injected with 2 nmol of OTL38 and image with IVIS imager at 2 hours post injection. Exposure time=1 s; Excitation: 745 nm. Emission: ICG (indocyanine green).
Figure 11B:
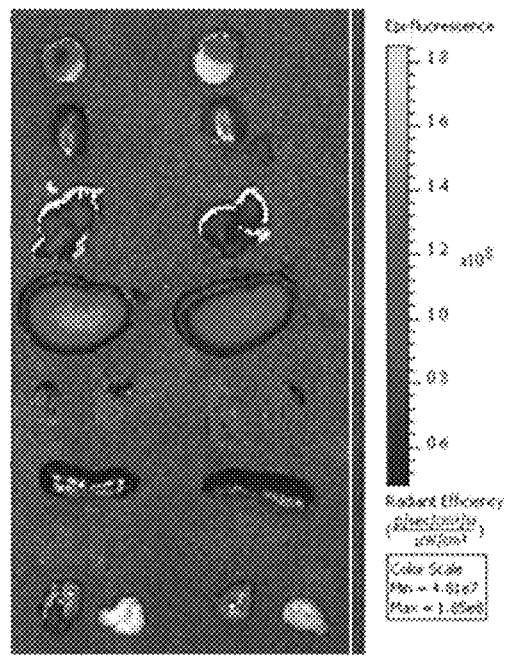
FIG. 11B depicts a tissue biodistribution analysis using fluorescence imaging of mice of FIG. 11A.
Figure 11C:
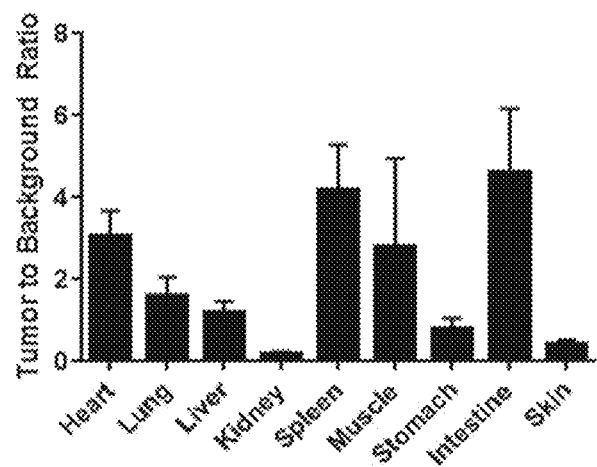
FIG. 11C depicts a tumor-to-tissue ratio from tissue biodistribution data of mice of FIG. 11C.

As seen in the FIG. 11A, OTL38 accumulated mainly in the FR-positive SKOV3 tumor xenografts, with no substantial fluorescence activity in the other tissues. To quantitate in vivo specificity of OTL38 to ovarian cancer, ex-vivo tissue biodistribution study was performed on the same animals that were subjected to whole body imaging. The highest fluorescence intensities were observed in FR-positive tumors and kidneys (FIG. 11B). All the other normal tissues displayed minimal levels or no uptake, resulting in excellent tumor-to-normal tissue ratios (FIG. 11C) especially given SKOV3 cells express low levels of FR-α.

(b) Ovarian Cancer Orthotopic Model

Figure 12A:
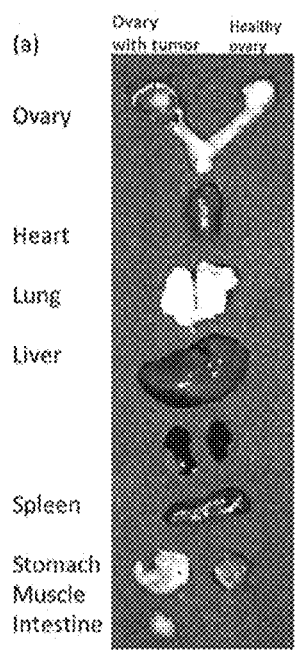
FIG. 12A depicts a tissue biodistribution analysis of overlay of fluorescence image over white light image (after adjusting the threshold) of selected tissues. Ovarian (SKOV3) orthotopic tissue biodistribution data of mouse injected with 2 nmol of OTL38 and image with IVIS imager at 2 hours post injection. Exposure time=1 s; Excitation: 745 nm. Emission: ICG (indocyanine green). Kidneys were removed from the biodistribution images.
Figure 12B:
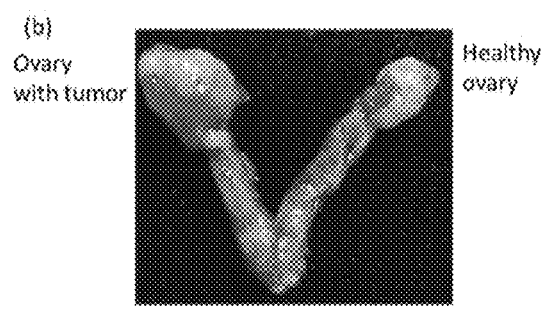
FIG. 12B depicts an image of ovarian orthotopic ovaries of mouse of FIG. 12A.
Figure 12C:
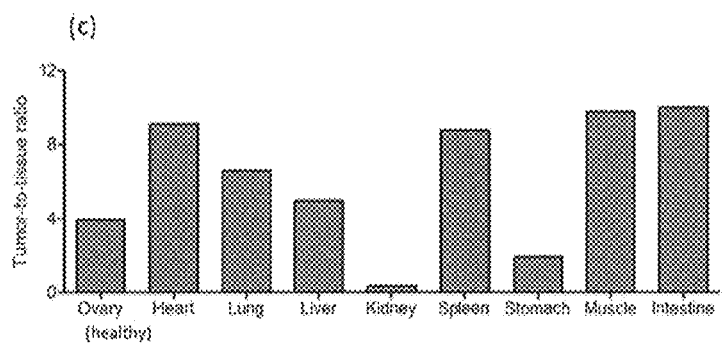
FIG. 12C depicts a tumor-to-tissue ratio from tissue biodistribution data of mouse of FIG. 12A.

As seen in the FIG. 12A, OTL38 accumulated mainly in the ovary with FR-positive SKOV3 orthotopic tumor and there was no substantial fluorescence activity in the healthy ovary or the other tissues except kidneys resulting in excellent tumor-to-normal tissue ratios (FIG. 12C) especially given SKOV3 cells have lower levels of FR-α.

Example 11

In Vivo Efficacy of OTL38 in a Breast Cancer (MDA-MB 231, a Human Ovarian Cancer Cell Line) Model that Express High Levels of FR-α

(a) Xenograft Tumor Model

Figure 13A:
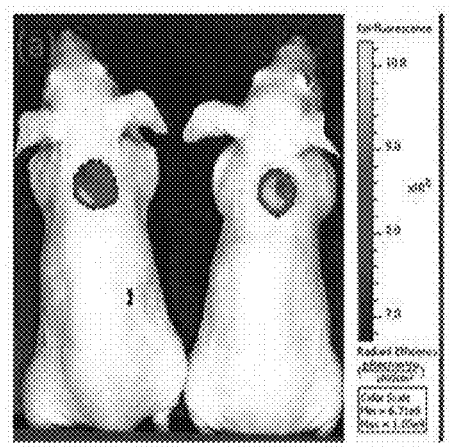
FIG. 13A depicts an overlay of whole body fluorescence image over white light image (after adjusting the threshold). Tissue biodistribution data of MDA-MB 231 xenograft breast cancer tumor bearing mice injected with 2 nmol of OTL38 and image with IVIS imager at 2 hours post injection. Exposure time=1 s; Excitation: 745 nm. Emission: ICG (indocyanine green).
Figure 13B:
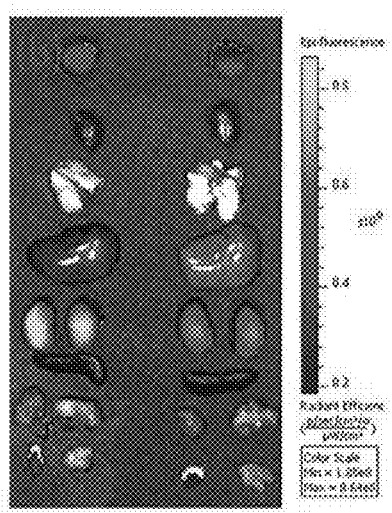
FIG. 13B depicts a tissue biodistribution analysis using fluorescence imaging of mice of FIG. 13A.
Figure 13C:
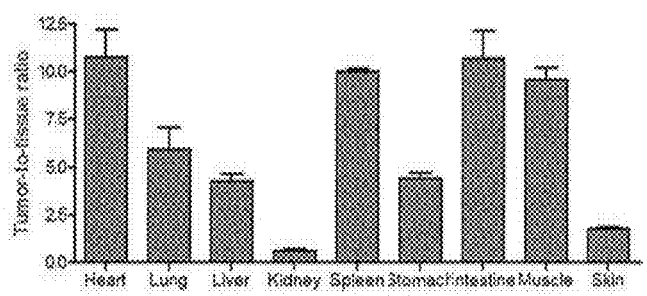
FIG. 13C depicts a tumor-to-tissue ratio from tissue biodistribution data of mice of FIG. 13A.

As seen in the FIG. 13A, OTL38 accumulated mainly in the FR-positive MDA-MB 231 tumor xenografts, with no substantial fluorescence activity in the other tissues. To quantitate in vivo specificity of OTL38 to breast cancer, ex-vivo tissue biodistribution study was performed on the same animals that were subjected to whole body imaging. The highest fluorescence intensities were observed in FR-positive tumors and kidneys (FIG. 13B). All the other normal tissues displayed minimal levels or no uptake, resulting in excellent tumor-to-normal tissue ratios (FIG. 13C).

(b) Orthotopic and Metastatic Models

Figure 14A:
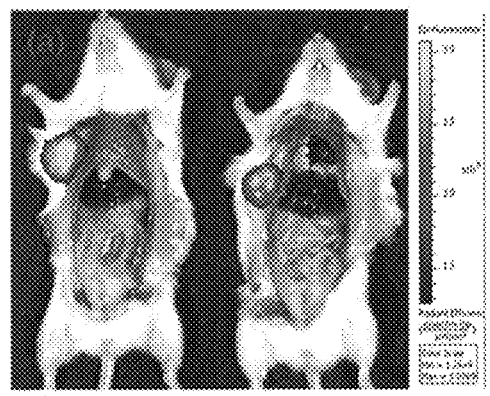
FIG. 14A depicts an overlay of whole body fluorescence image over white light image (after adjusting the threshold) of human breast tumor xenografts (MDA-MB 231). Tissue biodistribution data of human breast (MDA-MB 231) orthotopic tumor bearing mice injected with 2 nmol of OTL38 and image with IVIS imager at 2 hours post injection. Exposure time=1 s; Excitation: 745 nm. Emission: ICG (indocyanine green).
Figure 14B:
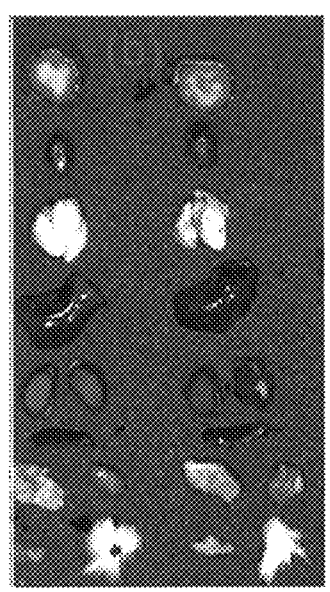
FIG. 14B depicts a tissue biodistribution analysis using fluorescence imaging of mice of FIG. 14A.
Figure 14C:
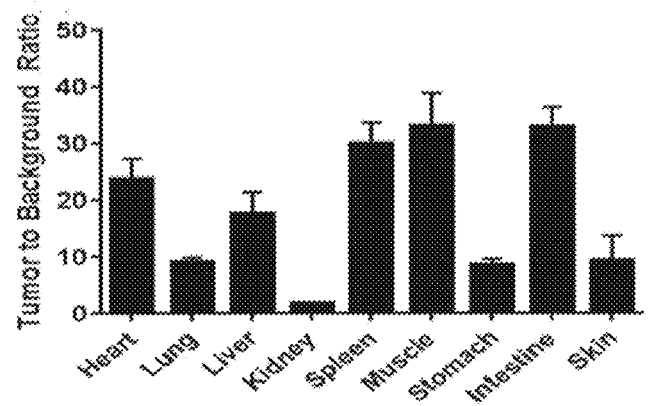
FIG. 14C depicts a tumor-to-tissue ratio from tissue biodistribution data of mice of FIG. 14A.
Figure 14D:
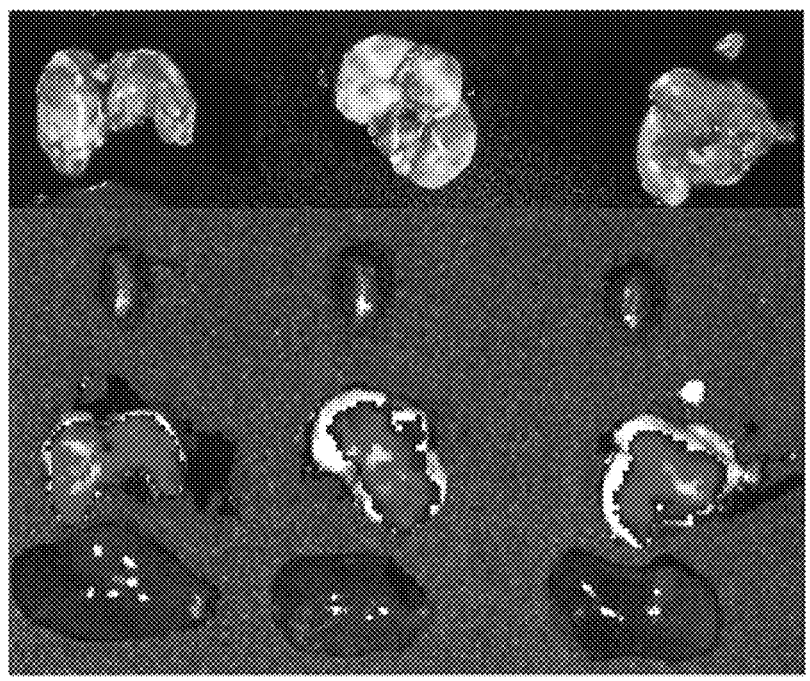
FIG. 14D depicts human breast cancer cells metastasized to lung.

As seen in FIG. 14A, OTL38 accumulated mainly in the FR-positive MDA-MB 231 orthotopic tumors, with no substantial fluorescence activity in the other tissues. To quantitate in vivo specificity of OTL38 to breast cancer, ex-vivo tissue biodistribution study was performed on the same animals that were subjected to whole body imaging. The highest fluorescence intensities were observed in FR-positive tumors and kidneys (FIG. 14B). All the other normal tissues including healthy memory pad and breast displayed minimal levels or no uptake, resulting in excellent tumor-to-normal tissue ratios (FIG. 14C).

As seen in the FIG. 14 (d), OTL38 mainly accumulated in the breast cancer cells metastasized to lung.

Example 12

Figure 15A:
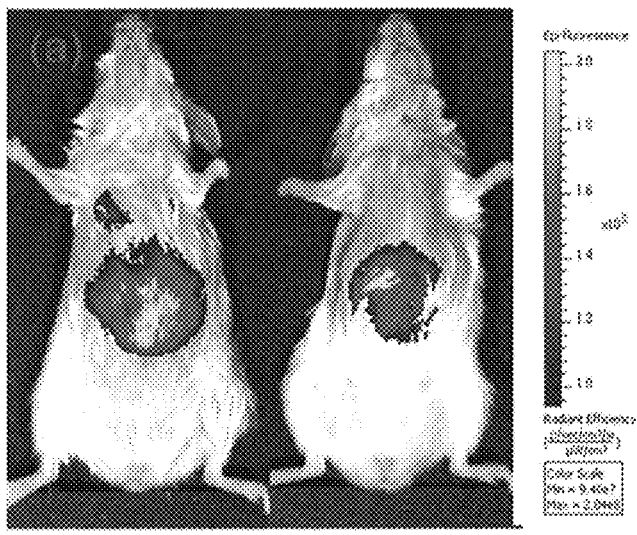
FIG. 15A depicts an overlay of whole body fluorescence image over white light image (after adjusting the threshold) a murine leukemia cells metastasized liver, lung and spleen. Tissue biodistribution data of a murine leukemia cancer (L1210A) metastatic tumor bearing mice injected with 2 nmol of OTL38 and image with IVIS imager at 2 hours post injection. Exposure time=1 s; Excitation: 745 nm. Emission: ICG (indocyanine green).
Figure 15B:
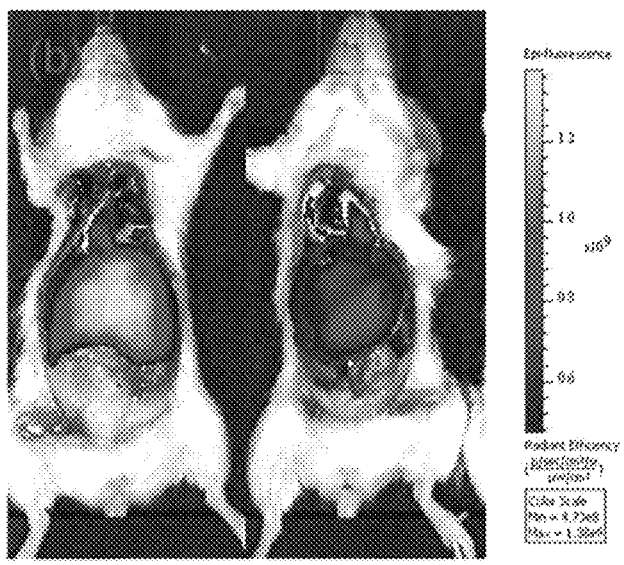
FIG. 15B depicts an overlay of whole body fluorescence image over white light image (after adjusting the threshold) of mice of FIG. 15A.
Figure 15C:
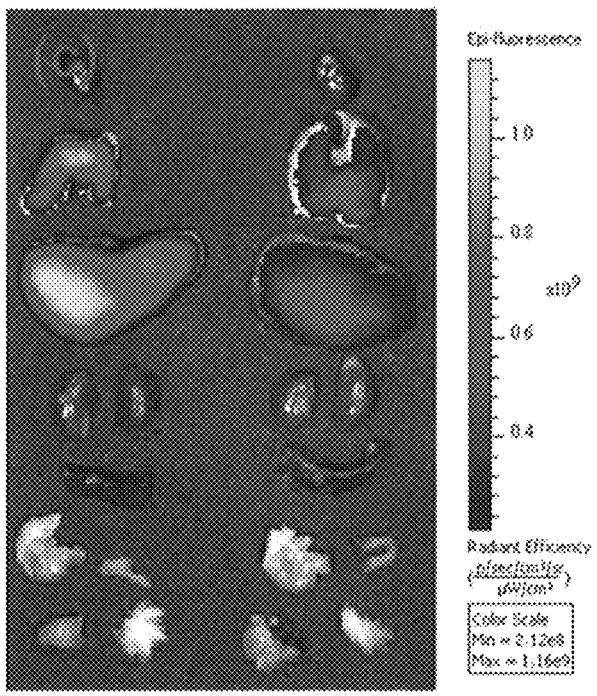
FIG. 15C depicts a tumor-to-tissue ratio from tissue biodistribution data of mice of FIG. 15A.

In Vivo Efficacy of OTL38 in a Leukemia Cancer Cells (L1210A, a Murine Leukemia Cancer Cell Line) Metastasized to Liver, Lung and Spleen As seen in the FIGS. 15A and 15B, OTL38 accumulated mainly in the FR-positive L1210A tumors metastasize to the liver, lung and spleen, with no substantial fluorescence activity in the other tissues. To quantitate in vivo specificity of OTL38 to breast cancer, ex-vivo tissue biodistribution study was performed on the same animals that were subjected to whole body imaging. All the other normal tissues including healthy memory fat pad and breast displayed minimal levels or no uptake, resulting in excellent tumor-to-normal tissue ratios (FIG. 15C).

Example 13

Figure 16A:
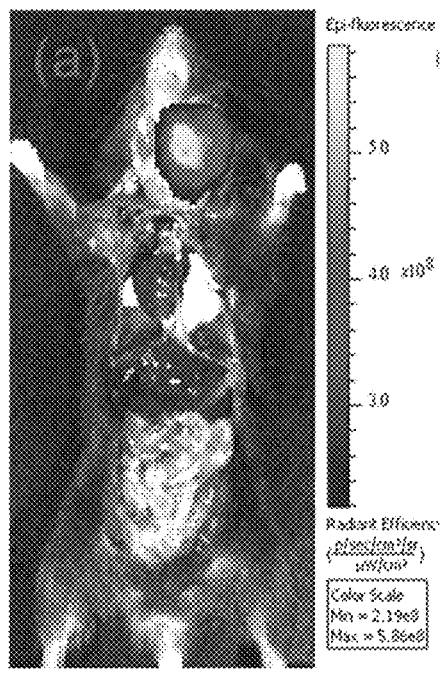
FIG. 16A depicts an overlay of whole body fluorescence image over white light image (after adjusting the threshold). Tissue biodistribution data of a murine lung cancer (M109) metastatic tumor bearing mice injected with 2 nmol of OTL38 and image with IVIS imager at 2 hours post injection. Exposure time=1 s; Excitation: 745 nm. Emission: ICG (indocyanine green).
Figure 16B:
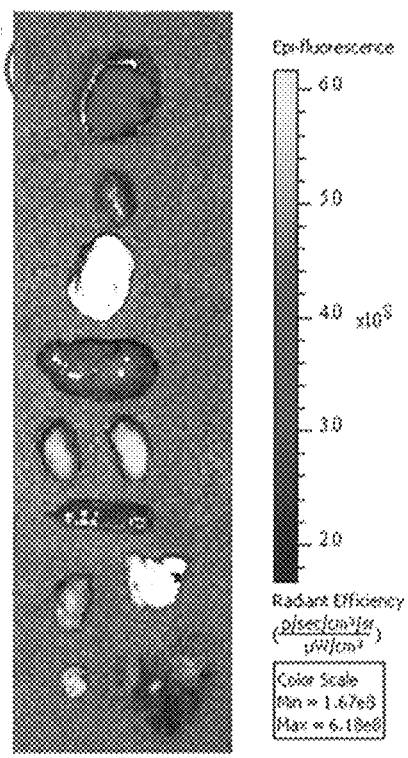
FIG. 16B depicts a tissue biodistribution analysis using fluorescence imaging of mice of FIG. 16A.

In Vivo Efficacy of OTL38 in a Lung Cancer Cells (M109, a Murine Lung Cancer Cell Line) Metastasized to Head & Neck As seen in the FIG. 16A, OTL38 accumulated mainly in the FR-positive M109 tumors metastasize to the liver, lung and spleen, with no substantial fluorescence activity in the other tissues. To quantitate in vivo specificity of OTL38 to breast cancer, ex-vivo tissue biodistribution study was performed on the same animals that were subjected to whole body imaging. All the other normal tissues including healthy memory fat pad and breast displayed minimal levels or no uptake, resulting in excellent tumor-to-normal tissue ratios.

Example 14

In Vivo Specificity of OTL38 for FR (a) Blocking the FR with Excess Folic Acid

Figure 17A:
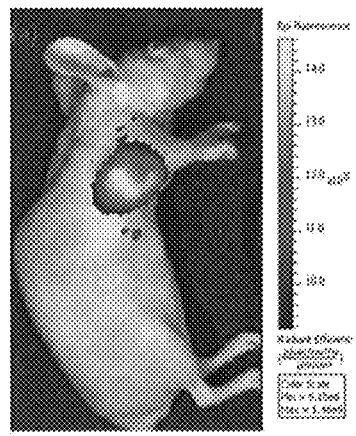
FIG. 17A depicts an overlay of whole body fluorescence image over white light image (after adjusting the threshold), 2 h after administering 2 nmol of OTL38 into a mouse bearing a human breast tumor xenograft. Images were acquired with IVIS imager at 2 h post injection. Exposure time=1 s; Excitation: 745 nm. Emission: ICG (indocyanine green).
Figure 17B:
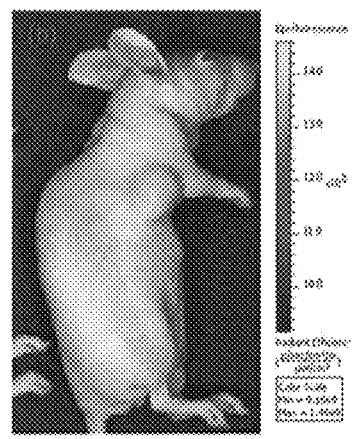
FIG. 17B depicts an overlay of whole body fluorescence image over white light image (after adjusting the threshold), 2 h after administering 100 fold excess of folic acid followed by 2 nmol of OTL38 into a mouse bearing a human breast tumor xenograft. Images were acquired with IVIS imager at 2 h post injection. Exposure time=1 s; Excitation: 745 nm. Emission: ICG (indocyanine green).
Figure 17C:
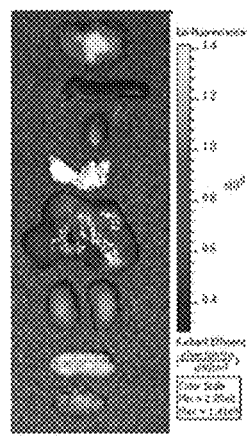
FIG. 17C depicts a tissue biodistribution of mice of FIG. 17A.
Figure 17D:
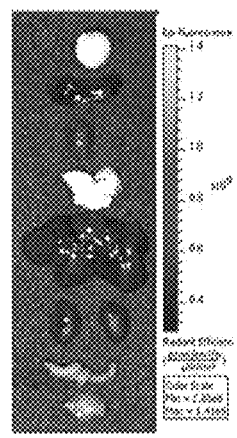
FIG. 17D depicts a tissue biodistribution of mice of FIG. 17B.

Both whole body imaging (FIGS. 17A and 17B) and tissue biodistribution images (FIGS. 7C and 7D) demonstrated that OTL38 mainly accumulated in FR-positive MDA-MB 231 tumor xenografts and kidneys. However, accumulation of the OTL38 in both organs was inhibited by the administration of 100 fold excess of folic acid prior to injection of OTL38 (FIGS. 17B and D) indicating that saturation of FR prevents the binding of OTL38 to folate receptor. Therefore, these data suggest that OTL38 is highly specific for FR.

(a) Administering to Tumor Xenografts (A549 Cells) that do not Express FR

Figure 18A:
FIG. 18A depicts an overlay of whole body fluorescence image over white light image (after adjusting the threshold) of a human lung tumor xenograft that do not express FR. Three mice from tissue biodistribution data of A549 tumor bearing mice injected with 2 nmol of OTL38 and image with IVIS imager at 2 hours post injection. Exposure time=1 s; Excitation: 745 nm. Emission: ICG (indocyanine green).
Figure 18B:
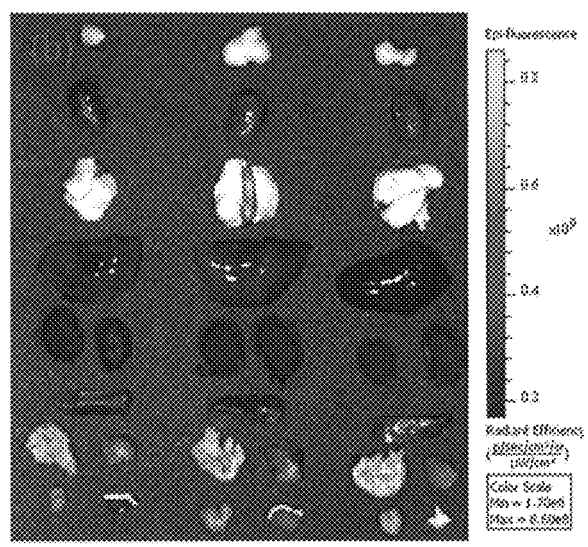
FIG. 18B depicts a tissue biodistribution of mice of FIG. 18A.

Whole body imaging of A549 tumor xenograft model demonstrated that OTL38 did not accumulated in the FR-negative tumors (FIG. 18A). Analysis of tissue biodistribution (FIG. 18B) demonstrated that, no fluorescence was observed in FR-negative tumors. As anticipated, kidney uptake was observed. Therefore, we can conclude that OTL38 is highly specific for FR and it will not passively accumulate in tumors that do not express FR.

4. CONCLUSIONS

In vitro cell binding studies using human cervical cancers demonstrated that OTL38 binds to FR with high affinity and specificity. In vivo whole body fluorescence imaging using a human ovarian cancer cell line tumor xenograft models showed that OTL38 mainly accumulate in the FR-positive tumor xenografts and kidneys. Ex vivo tissue biodistribution of same mice that we subjected to whole body imaging confirmed that OTL38 binds to FR-positive tumors and kidneys with minimal or no uptake in other healthy tissues resulting in excellent tumor-to-background ratios. Ex vivo biodistribution data from orthotopic ovarian model demonstrated that OTL38 mainly accumulated in the ovary with a human ovarian tumor but not in the healthy ovary or other tissues. Administration of OTL38 to either FR-negative tumor xenograft model or by blocking the FR in FR-positive tumor xenograft model further verified specify and selectivity of OTL38 to FR.

The most suitable route for administration will vary depending upon the disease state to be treated, or the location of the suspected condition or tumor to be diagnosed. For example, for treatment of inflammatory conditions and various tumors, local administration, including administration by injection directly into the body part to be irradiated by the excitation light (e.g., intracavitarily) provides the advantage that the targeting construct (e.g., fluorescently tagged antibodies) can be administered in a high concentration without risk of the complications that may accompany systemic administration thereof.

The compounds of the present disclosure as well as any additional targeting constructs used in diagnostic cocktails comprising the compounds of the present disclosure are administered in a "effective amount" for diagnosis. An effective amount is the quantity of a targeting construct necessary to aid in direct visualization of any target tissue located in the body part under investigation in a subject. A "subject" as the term is used herein is contemplated to include any mammal, such as a domesticated pet, farm animal, or zoo animal, but preferably is a human. Amounts effective for diagnostic use will, of course, depend on the size and location of the body part to be investigated, the affinity of the targeting construct for the target tissue, the type of target tissue, as well as the route of administration. Local administration of the targeting construct will typically require a smaller dosage than any mode of systemic administration, although the local concentration of the targeting construct may, in some cases, be higher following local administration than can be achieved with safety upon systemic administration.

Since individual subjects may present a wide variation in severity of symptoms and each targeting construct has its unique diagnostic characteristics, including, affinity of the targeting construct for the target, rate of clearance of the targeting construct by bodily processes, the properties of the fluorophore contained therein, and the like, the skilled practitioner will weigh the factors and vary the dosages accordingly.

The compounds of the present disclosure as well as cocktails comprising these compounds can be formulated as a sterile injectable suspension according to known methods using suitable dispersing or wetting agents and suspending agents. The sterile injectable preparation may also be a sterile injectable solution or suspension in a non-toxic parenterally-acceptable diluent or solvent, for example, as a solution in 1-4, butanediol. Sterile, fixed oils are conventionally employed as a solvent or suspending medium. For this purpose any bland fixed oil may be employed, including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate, or the like. Buffers, preservatives, antioxidants, and the like, can be incorporated as required, or, alternatively, can comprise the formulation.

It will be apparent to those skilled in the art that various changes may be made in the disclosure without departing from the spirit and scope thereof, and therefore, the disclosure encompasses embodiments in addition to those specifically disclosed in the specification, but only as indicated in the appended claims.

The examples that follow are merely provided for the purpose of illustrating particular embodiments of the disclosure and are not intended to be limiting to the scope of the appended claims. As discussed herein, particular features of the disclosed compounds and methods can be modified in various ways that are not necessary to the operability or advantages they provide. For example, the compounds can incorporate a variety of amino acids and amino acid derivatives as well as targeting ligands depending on the particular use for which the compound will be employed. One of skill in the art will appreciate that such modifications are encompassed within the scope of the appended claims.

The invention claimed is:

1. A method of imaging a carcinoma that expresses a folate receptor comprising the steps of:
    a. administering to a patient in need of an effective amount of a compound capable of binding to a cancerous cell having the formula:

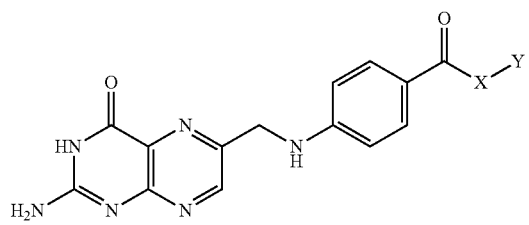

or a pharmaceutically acceptable salt or isotope thereof, wherein: X is an single amino acid or a single amino acid derivative thereof, wherein the single amino acid or single amino acid derivative contains an —OH, —NH$_2$, or —SH functional group, and Y is a dye that has a fluorescence excitation and emission spectra in the near infra-red range, wherein Y is represented by the formula:

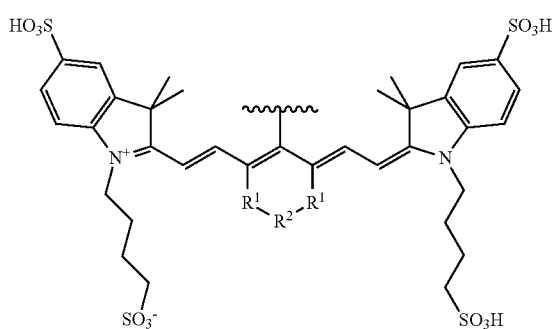

wherein, $R^1$ is independently selected from the group consisting of O, S, N and C, and $R^2$ is independently selected from the group consisting of $CH_2$ and $CH_2CH_2$, and the compound enhances the fluorescence of the dye, Y; and b. fluorescent imaging of an area of concern in the patient's body where the compound has been bound to a cancerous cell wherein the carcinoma is selected from the group consisting of cervical cancer, ovarian cancer, breast cancer, leukemia cancer, and lung cancer.

2. The method of claim 1 wherein the single amino acid of the compound is selected from the group consisting of tyrosine, cysteine, serine, and lysine.

3. The method of claim 1 wherein the single amino acid of the compound is tyrosine.

4. The method of claim 1 wherein the single amino acid derivative is selected from the group consisting of a derivative of tyrosine, a derivative of cysteine, a derivative of serine and a derivative of lysine.

5. The method of claim 1 wherein the patient is a human.

* * * * *

UNITED STATES PATENT AND TRADEMARK OFFICE
CERTIFICATE OF CORRECTION

PATENT NO. : 9,789,208 B2  
APPLICATION NO. : 15/259719  
DATED : October 17, 2017  
INVENTOR(S) : Sumith A. Kularatne Page 1 of 1

It is certified that error appears in the above-identified patent and that said Letters Patent is hereby corrected as shown below:

In the Claims

Column 37, Line 16, Claim 1, delete "and C," and insert -- ,C and $CH_2$, --.

Signed and Sealed this  
First Day of July, 2025

Coke Morgan Stewart  
*Acting Director of the United States Patent and Trademark Office*